US007371414B2

(12) United States Patent
Sellers et al.

(10) Patent No.: US 7,371,414 B2
(45) Date of Patent: May 13, 2008

(54) THERAPEUTIC AND DIAGNOSTIC METHODS DEPENDENT ON CYP2A ENZYMES

(75) Inventors: Edward Sellers, Toronto (CA); Rachel Tyndale, Toronto (CA)

(73) Assignee: Nicogen, Inc., Toronto (CA)

( * ) Notice: Subject to any disclaimer, the term of this patent is extended or adjusted under 35 U.S.C. 154(b) by 0 days.

(21) Appl. No.: 11/682,505

(22) Filed: Mar. 6, 2007

(65) Prior Publication Data

US 2007/0254921 A1 Nov. 1, 2007

Related U.S. Application Data

(60) Continuation of application No. 10/815,995, filed on Apr. 2, 2004, now abandoned, which is a division of application No. 09/584,669, filed on Jun. 1, 2000, now Pat. No. 6,908,631, which is a continuation of application No. PCT/CA98/10193, filed on Dec. 1, 1998.

(60) Provisional application No. 60/107,392, filed on Nov. 6, 1998, provisional application No. 60/084,847, filed on May 8, 1998, provisional application No. 60/067,021, filed on Dec. 1, 1997, provisional application No. 60/067,020, filed on Dec. 1, 1997.

(51) Int. Cl.
*A01N 65/00* (2006.01)
(52) U.S. Cl. .................................................... 424/725
(58) Field of Classification Search ..................... None
See application file for complete search history.

(56) References Cited

U.S. PATENT DOCUMENTS

| 5,653,987 | A | 8/1997 | Modi et al. |
| 5,760,049 | A | 6/1998 | Viner |
| 6,908,631 | B1 | 6/2005 | Sellers et al. |
| 2002/0019421 | A1 | 2/2002 | Biberman |
| 2002/0168403 | A1 | 11/2002 | Biberman |
| 2005/0032844 | A1 | 2/2005 | Sellers |

FOREIGN PATENT DOCUMENTS

| WO | WO9004387 | 5/1990 |
| WO | WO9503050 | 2/1995 |
| WO | WO9534679 | 12/1995 |

OTHER PUBLICATIONS

Berkman, et al., "In Vitro-In Vivo Correlations of Human (S)-Nicotine Metabolism", Biochemical Pharmacology, vol. 50, No. 4. pp. 565-570, 1995, Pergamon, Mar. 6, 1995.
Cashman, et al., "Metabolism of Nicotine by Human Liver Microsomes: Stereoselective Formation of trans-Nicotine N'-Oxide", Chem. Res. Toxicol, 1992, 5, 639-646, 1992.
Fernandez-Salguero, et al. "A Genetic Polymorphism in Coumarin 7-Hydroxylation: Sequence of the Human CYP2A Genes and Identification of Variant CYP2A6 Alleles", Am. J. Hum. Genet. 57:651-660, Jun. 1, 1995.
McCracken, et al., "Cotinine Formation by cDNA-expressed Human Cytochromes P450", Med. Sci. Rev., 1992, 20, 877-878.
Seaton, et al., "Variable Affecting Nicotine Metabolism", Pharmac. Ther. vol. 60, pp. 461-500, Pergamon, 1993.
Fowler, et al., "Brain Monoamine Oxidase A Inhibition in Cigarette Smokers", Proc. Natl. Acad. Sci. USA, vol. 93, pp. 14065-14069, Nov. 1996.
Tiano, et al., "Human CYP2A6 Activation of 4-(methylnitrosamino)-1-(3-pyridyl)-1-butanone (NNK): Mutational Specificity in gpt Gene of AS52 Cells", Carcinogenesis, vol. 15, No. 12, pp. 2859-2866, 1984.
J. Invest. Med., vol. 44, No. 1, p. 120A, 1996.
Notice of Opposition to a European Patent, Patent No. 1033979B1 to Nicogen Inc.
Zhang, W. et al., "Specificity and Selectivity of Tranylcypromine and Methoxsalen Inhibition of Cytochrome P450s in Vitro", http://www.utoronto.ca/grdpharm/zhang.html, May 20, 1999.
Tyndale, R.F. et al., "Inhibition of Nicotine's Metabolism: A Potential New Treatment for Tobacco Dependence", Clinical Pharmaceology & Therapeutics, vol. 65, No. 2, p. 145: Ol-A-1, 1999.
Sellers, E.M. et al. "Inhibition of CYP2A6 Decreases Smoking", Clinical Pharmacology & Therapeutics, vol. 65, No. 2, p. 153: PI1-26. 1999.

(Continued)

*Primary Examiner*—Michael Meller
(74) *Attorney, Agent, or Firm*—Bereskin & Parr; Patricia Folkins

(57) ABSTRACT

A method of regulating the activity of human cytochrome P450 isozyme CYP2A6 to control nicotine metabolism or decrease to production of carcinogens from procarcinogens, such as those present in tobacco smoke, in an individual by selectively inhibiting CYP2A6. Various prophylactic (i.e., prevention and treatment) compositions and methods are also described, including an improved oral nicotine composition and method comprising the use of nicotine together with an inhibitor of the CYP2A6 enzyme.

Furthermore, it has been discovered that the presence in an individual of a mutant allele of human cytochrome P450 enzyme CYP2A6 (referred to throughout this specification as "CYP2A6" for brevity) is predictive of an individual who: (i) has a decreased risk of becoming a smoker, (ii) will smoke less if he/she becomes dependent, and/or (iii) may be at relatively lower risk for cancer due to both decreased smoke exposure and decreased CYP2A6-mediated activation of tobacco smoke and other procarcinogenic substrates. This invention provides diagnostic methods for predicting tobacco dependence risk and risk for cancers related to CYP2A6 substrates in an individual by analysing for the presence of a mutant genotype for human cytochrome P450 enzyme CYP2A6 in an individual, ranging from gene duplication (multiple copies of CYP2A6) to single or even no copies due to null alleles or gene deletion.

9 Claims, 23 Drawing Sheets-

OTHER PUBLICATIONS

Sellers, E.M. et al., "Mimicking Gene Defects to Treat Drug Dependence", Annals of the New York Academy of Sciences, (2000) 909:233-246.

Draper, A.J. et al., "Inhibition of Coumarin 7-Hydroxylase Activity in Human Liver Microsomes", Archives of Biochemistry and Biophysics, (1997) vol. 341, No. 1, pp. 47-61.

Chauret, N. et al., "In Vitro Comparison of Cytochrome P450-Mediated Metabolic Activities in Human, Dog, Cat and Horse", Drug Metabolism and Disposition, vol. 25, No. 10.

George, T.P. et al., "A Preliminary Placebo-Controlled Trial of Selegiline Hydrochloride for Smoking Cessation", 2003, Biol. Psychiatry, vol. 53, pp. 136-143.

Fowler, J.S. et al., "Inhibition of Monoamine Oxidase B in the Brains of Smokers", 1996, Nature, vol. 379, pp. 733-736.

Nakajima, M. et al., "Characterization of CYP2A6 Involved in 3'-hydroxylation of Continine in Human Liver Microsomes", J. Pharmacol. Exp. Therap., (1996) vol. 277, No. 2, pp. 1010-1015.

Nakajima, M. et al., "Role of Human Cytochrome P4502A6 in C-oxidation of Nicotine", Drug Metabol. Dospos., (1996) vol. 24, No. 11, pp. 1212-1217.

Tsujimoto, A et al., "Potent Inhibitory Action of Pilocarpine on Hepatic Drug Metabolism", Jpn. J. Pharmacol., (1972) vol. 22, No. 5, 736.

Tsujimoto, A. et al., "A Study of the Nature of Pilocarpine on Hepatic Drug-Metabolizing Enzymes", Biochem. Pharmacol., (1977) vol. 26, No. 21, pp. 2072-2074.

Foth, H. et al., "Nicotine Metabolism is Isolated Perfused Lung and Liver of Phenobarbital and Benzoflavone-Treated Rats", Arch. Toxicol., (1991) vol. 65, No. 1, pp. 68-72.

Kyerematen, G. A., et al., "Metabolism of Nicotine by Hepatocytes", Biochem. Pharmacol., (1990) vol. 40, No. 8, pp. 1747-1756.

Yamazaki, H. et al., "Cytochrome P450 sE1 and 2A6 Enzymes as Major Catalysts for Metabolic Activation of N-nitrosodialkylamines and Tobacco-Related Nitorsamines in Human Liver Microsomes", Carcinogenesis (1992) vol. 13, No. 10, pp. 1789-1794.

CAPLUS, DN 120:238085, Gamitskij et al., SU 1803032 A1, Mar. 23, 1993, English abstract with notes from oral translation.

Mays et al., "Methoxsalen is a Potent Inhibitor of Caffeine in Humans", Clin. Pharmacol. Ther., 42:621-626 (1987).

Maenpaa et al., "Metabolic Interactions of methoxsalen and Coumarin in Humans and Mice", Biochem. Pharmacol., 48(7), (1994), 1363-9.

Benowitz, N.L. et al., "Deficient C-Oxidationof Nicotine", Clinical Pharmacol. and Therap., 57(5):590-594 (1995) (Abstract).

Pilocarpine

Nicotine 4,4'-Methylene bis[2-chloroaniline

6-Aminochrysene

α-Naphthoflavone naringenin naringin

Dicumarol
About 80% activity left at 0.05 mM concentration

4-Chromanone  4-Chromanol

1-Naphthol

70% inhibition at
0.5 mM concentration 1,3-Indandione   1,Indanone

Warfarin

Sphondin          Amgelicin         Pimpinrllin
IC50 90           IC 50 160         IC50>500

$(CH_3CH_2)_2NCS_2NH_4$

Diethyldithiocarbamic acid
ammonium salt

SM-12502

$[(CH_3)_2N]_3P(O)$

Hexamethylphosphoramide $(CH_3)_2NNO$

N-Nitrosodimethylamine

FIGURE 2D

Non-selective MAO inhibitors

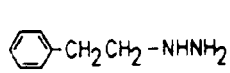
Pheneizine

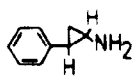
Tranylcypromine

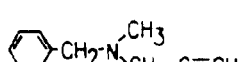
Pargyline

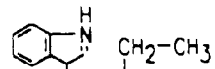
Etryptamine

Selective MAO Inhibitors

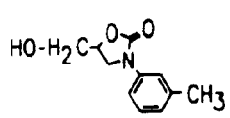
MAO-A inhibitor: Toloxatong

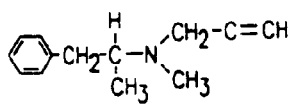
MAO-B inhibitor: Selegiline

Antidepressants

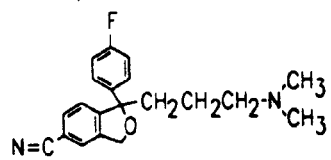
5-HT uptake inhibitor: citalopram

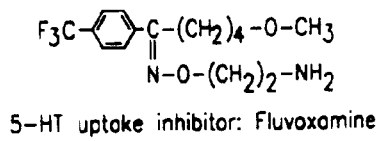
5-HT uptake inhibitor: Fluvoxamine

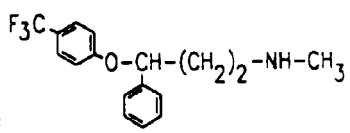
5-HT inhibitor: fluoxetine

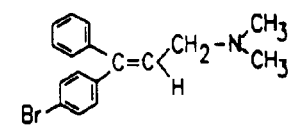
5-HT uptake inhibitor: Zimeldine

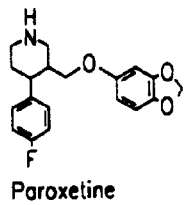
Paroxetine

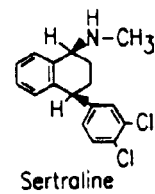
Sertraline

Others

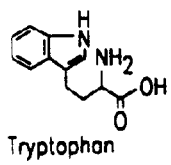
Tryptophan

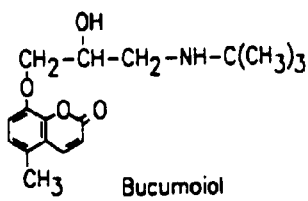
Bucumolol

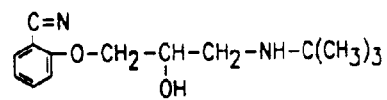
Bunitrolol

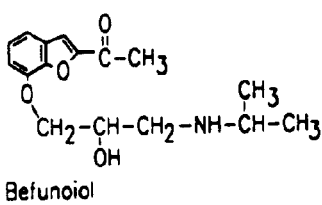
Befunolol

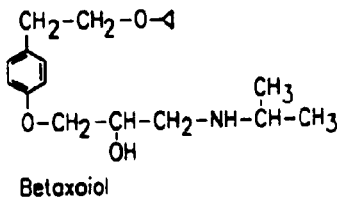
Betaxolol

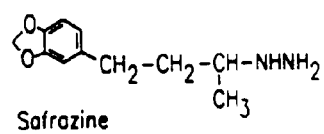
Safrazine

Estimated Ki = 1 uM
Calculated by PCS program Ki = 1.1 uM

Estimated Ki = 2 uM
Calculated by PCS program Ki = 1.6 uM

SEQUENCE LISTING

```
<160> NUMBER OF SEQ ID NOS: 4

<210> SEQ ID NO 1
<211> LENGTH: 32
<212> TYPE: DNA
<213> ORGANISM: artificial sequence
<220> FEATURE:
<223> OTHER INFORMATION: Primer

<400> SEQUENCE: 1
cctcccttgc tggctgtgtc ccaagcttag gc                                    32

<210> SEQ ID NO 2
<211> LENGTH: 31
<212> TYPE: DNA
<213> ORGANISM: artificial sequence
<220> FEATURE:
<223> OTHER INFORMATION: Primer

<400> SEQUENCE: 2 cgcccttcc tttccgccat cctgccccca g                                     31

<210> SEQ ID NO 3
<211> LENGTH: 20
<212> TYPE: DNA
<213> ORGANISM: artificial sequence
<220> FEATURE:
<223> OTHER INFORMATION: Primer
```

```
<400> SEQUENCE: 3
gcgtggtatt cagcaacggg                                              20

<210> SEQ ID NO 4
<211> LENGTH: 18
<212> TYPE: DNA
<213> ORGANISM: artificial sequence
<220> FEATURE:
<223> OTHER INFORMATION: Primer

<400> SEQUENCE: 4
tcgtgggtgt tttccttc                                                18
```

THERAPEUTIC AND DIAGNOSTIC METHODS DEPENDENT ON CYP2A ENZYMES

This application is a continuation application of U.S. patent application Ser. No. 10/815,995 filed on Apr. 2, 2004 now abandoned, which is a divisional application of U.S. patent application Ser. No. 09/584,669 filed on Jun. 1, 2000 now U.S. Pat. No. 6,908,631 which is a national stage of international application No. PCT/CA98/10193 filed on Dec. 1, 1998, which claims the benefit of provisional patent applications U.S. 60/067,020 filed on Dec. 1, 1997, U.S. 60/067,021 filed on Dec. 1, 1997, U.S. 60/084,847 filed on May 8, 1998 and U.S. 60/107,392 filed on Nov. 6, 1998. The contents of all of the above-mentioned applications are incorporated herein by reference in their entirety.

FIELD OF THE INVENTION

The invention relates to methods and compositions for regulating nicotine metabolism in an individual; methods and compositions for enhancing nicotine replacement therapies; methods and compositions for diagnosing tobacco risk dependence and risk for cancers and methods for treating or preventing cancer.

REVIEW OF THE ART

Nicotine is one of the most widely used psychoactive drugs in the world. The World Health Organization reports that there are currently in excess of 1 billion smokers worldwide, or roughly one-third of the global population aged 15 years and older. It is well established that smoking is associated with a higher incidence of many diseases, including various types of cancers, respiratory diseases, cardiovascular diseases, gastrointestinal disorders, as well as many other medical complications (Lee et al., *Arch. Intern. Med.*, "Cigarette smoking, nicotine addiction, and its pharmacologic treatment," 153(1): 34-48 (1993)).

Nicotine is the primary compound present in tobacco that is responsible for establishing and maintaining tobacco dependence (Henningfield et al., *J. Pharmacol. Exp. Ther.*, "Abuse liability and pharmacodynamic characteristics of intravenous and inhaled nicotine," 234(1): 1-12 (1985)). Specifically, it has been established in the art that dependent smokers adjust their smoking behaviour to maintain central nicotine levels (McMorrow M J, et al., "Nicotine's role in smoking: an analysis of nicotine regulation," *Psychological Bulletin*, 93(2):302-27 (1983); Russell M S H, "Nicotine intake and its regulation by smokers. Tobacco smoking and nicotine," *Advances in behavioural biology*, Martin W R, et al., New York, Plenum Press, 31:25-50 (1987)). It has been further established that: (i) smoking increases if nicotine content in cigarettes is decreased (Benowitz N L, "Drug Therapy. Pharmacologic Aspects of Cigarette Smoking and Nicotine Addiction," *New Engl. J. Med.*, 319(20): 1318-30 (1988)), (ii) smoking increases if nicotine excretion is increased by urine acidification (Benowitz N L, "The Use of Biologic Fluid Samples in Assessing Tobacco Smoke Consumption," *NIDA Res. Monogr.*, 48:6-26 (1983)), and (iii) smoking decreases with administration of nicotine via concurrent I.V. or patch nicotine (Benowitz, N L et al., "Nicotine Metabolic Profile in Man: Comparison of Cigarette Smoking and Transdermal Nicotine", *J. Pharmacol. Exp. Ther.*, 268(1):296-303 (1994); and Benowitz, N L et al., "Intravenous Nicotine Replacement Suppresses Nicotine Intake From Cigarette Smoking", *J. Pharmacol. Exp. Ther.*, 254(3):1000-5 (1990)).

In light of the key role of nicotine in producing tobacco dependence and regulating smoking behaviour, it is important to understand the pattern of nicotine metabolism and the sources of variation of this metabolism in humans.

In humans, 60-85% of nicotine is metabolized to the inactive metabolite cotinine (Benowitz, et al. 1994). The cytochrome P450 (CYP) system has been implicated in the metabolism of nicotine. Evidence for CYP involvement in nicotine metabolism has come from rat liver studies in which reconstituted purified CYPs, and specific antibodies were shown to inhibit nicotine metabolism. In particular, rat studies have shown that phenobarbital inducible CYPs (i.e., the CYPs; -2B1, -2B2, -2C6, and -3A2) are involved in nicotine metabolism. Of 12 human CYPs forms tested, CYP2B6 showed the highest nicotine oxidase activity while CYP2E1 and CYP2C9 showed intermediate levels (Flammang et al., "Nicotine metabolism by cDNA-expressed human cytochrome P-450s," *Biochem. Arch.*, 8:1-8 (1992)). cDNA studies have implicated CYP2B6, CYP2C9, CYP2D6 and CYP2E1 and have provided a possible role for CYP2A6 in nicotine metabolism in isolated expression systems (Flammang et al., 1992; McCracken et al., "Cotinine formation by cDNA-expressed human cytochromes P450," *Med. Sci. Res.*, 20:877-878 (1992)).

In copending International patent application Ser. No. PCT/CA97/00506 (filed Jul. 17, 1997), the contents of which are hereby incorporated by reference, the present inventors teach that the genetically polymorphic CYP2A6 enzyme is the major enzyme responsible for this metabolic conversion. In human populations there is considerable interindividual variability in hepatic CYP2A6 function measured in vivo and in vitro (Yamano S, et al., "The CYP2A3 gene product catalyzes coumarin 7-hydroxylation in human liver microsomes," *Biochemistry*, 29:1322-1329 (1990); Cholerton S, et al., "Comparison of a novel thin-layer chromatographic-fluorescence detection method with a spectrofluorometric method for the determination of 7-hydroxycoumarin in human urine," *Journal of Chromatography*, 575(2):325-30 (1992); Rautio A, et al., "Interindividual variability of coumarin 7-hydroxylation in healthy volunteers," *Pharmacogenetics* 2(5):227-33 (1992); and Iscan et al., "Interindividual variability of coumarin 7-hydroxylation in a Turkish population," *Eur. J. Clin. Pharmacol.* 47(4): 315-318 (1994)).

Tobacco products are vehicles for the delivery of nicotine to the bloodstream which quickly carries nicotine to the brain and other organs. Nicotine produces many physiological and behavioural effects, including alteration of brain chemistry and function, which leads to an individual's dependence on nicotine. Dependent smokers adjust their smoking behaviour to regulate nicotine in the brain and body. Evidence includes increased smoking if nicotine content in cigarettes is decreased (Benowitz 1988), increased smoking if nicotine excretion is increased by urine acidification (Benowitz 1983), and decreased smoking with concurrent I.V. or patch nicotine (Benowitz, et al. 1994; Benowitz N L, et al. 1990).

While the art has made strides in gaining an understanding of the pattern of nicotine metabolism and the sources of variation of this metabolism in humans, there is still room for improvement. One area which has received little or no attention is in the diagnosis of risks for smoking and tobacco-related cancers, for example in non-smokers of relatively young age. In particular, it would be desirable to have a means by which it would be possible to readily identify individuals who: (i) have a decreased risk of becoming smokers, (ii) smoke less if they become dependent, and/or (iii) may be at relatively lower risk for cancer due to both decreased smoke exposure and decreased enzyme-mediated activation of tobacco smoke procarcinogens.

Other than nicotine dependence as a result of tobacco use, nicotine itself is not considered hazardous, namely it is not considered to be a causative agent in cancer and heart and lung disease. It is the other products which are found in tobacco products which are considered to be harmful, including combustion products such as carbon monoxide, gases and tar.

Nicotine replacement therapies (also referred to throughout this disclosure as "NRT's") are used to deliver nicotine to individuals in an attempt to assist an individual in abstaining from tobacco products. Recently, in a United Nations Conference on Trade and Development, entitled "Roundtable on Social and Economic Aspects of Reduction of Tobacco Smoking by Use of Alternative Nicotine Delivery Systems", Sep. 22-24, 1997, in an attempt to reduce tobacco-related morbidity and mortality, it was recommended that nicotine replacement therapies be made more easily available than tobacco.

Smoking tobacco products amount to a rapid delivery mechanism of nicotine to the bloodstream since almost all of the nicotine absorbed from tobacco smoke reaches systemic circulation without the need to initially pass through liver. For this reason, conventional nicotine replacement therapies have been based on the use of a delivery system (e.g., transdermal, etc.) which will systemically deliver nicotine.

Unfortunately, current commercially available NRT's are relatively inconvenient to use and administer, and are not liked by many patients. For example, transdermal (e.g., transdermal, chewing gum, etc.) NRT's are associated with occasional skin irritation and chewing gum (and other buccal delivery systems) NRT's are perceived as having a bad taste. Further, transdermal and chewing gum NRT's are plagued by the delivery of inconsistent nicotine levels to the patient. Still further, alternative delivery NRT systems such as inhalers and nasal sprays have failed to achieve patient acceptability.

Of note is that, to the knowledge of the inventors, an oral nicotine replacement therapy is not currently commercially available. While not wishing to be bound by any particular theory or mode of action, the reason for this is believed to be as follows. Oral nicotine must first pass through the liver before entering the systemic circulation. As a result, extensive metabolism of nicotine occurs. In particular, oral nicotine is about 60-85% metabolized from nicotine to continue by the liver so only 15-40% of oral nicotine reaches the systemic circulation (Benowitz, et al., "Stable isotope studies of nicotine kinetics and bioavailability," *Clin. Pharmacol. Ther.*, 49(3):270-7 (1991); Svensson, "Clinical pharmacokinetics of nicotine," *Clin. Pharmacokinet.*, 12(I):30-40 (1987); and Zins, et al., "Pharmacokinetics of nicotine tartrate after single-dose liquid enema, oral, and intravenous administration," *J. Clin. Pharmacol.*, 37(5):426-36 (1997)). Because the first-pass metabolism of nicotine is so effective and high concentrations of nicotine can not be used without irritating the digestive system, oral administration (e.g., a pill) has, heretofore, been an ineffective delivery system for nicotine. In light of this, there is no known effective oral nicotine replacement therapy. It would be desirable to have such a therapy since it would be much more convenient for the patient and would be more precisely controlled by the physician (e.g., prescribing dosage based on body weight and related factors which are difficult to take into account when prescribing nicotine patch or chewing gum).

SUMMARY OF THE INVENTION

The present inventors have found that variation in nicotine metabolism among individuals is due to variable expression of CYP2A isozymes; CYP2A6 has been shown to be the major nicotine metabolizing enzyme in human livers. Coumarin, a specific CYP2A6 substrate, was found to specifically and selectively inhibit nicotine metabolism to cotinine by 84%±11% in test livers, and addition of orphenadrine (a CYP2B6 inhibitor) enhanced the inhibition. Methoxsalen and tranylcypromine have also been found to be potent inhibitors of CYP2A6 and thus of nicotine to cotinine metabolism. The data indicate that variability in CYP2A6 expression results in inter-individual variation in nicotine metabolism, which in turn, can have behavioural consequences such as smoking more or less cigarettes. Therefore, inhibitors of CYP2A6 can be used to regulate nicotine metabolism, and in particular substantially decrease nicotine metabolism, thereby affecting tobacco use.

Broadly stated, the present invention relates to the diagnosis, prophylaxis and treatment of conditions requiring a reduction in the activity of a human cytochrome P450 enzyme CYP2A (referred to as "CYP2A" for brevity). The term "CYP2A" as used herein means all isoforms of CYP2A including but not limited to CYP2A(CYP1), CYP2A6, CYP2A7, CYP2A12, CYP2A13 and CYP2A16. Preferably the enzyme is CYP2A6.

The inventors have determined that the presence in an individual of a mutant allele of human cytochrome P450 enzyme CYP2A6 (referred to throughout this specification as "CYP2A6" for brevity) is predictive of an individual who: (i) has a decreased risk of becoming a smoker, (ii) will smoke less if he/she becomes dependent, and/or (iii) may be at relatively lower risk for cancer due to both decreased smoke exposure and decreased CYP2A6-mediated activation of tobacco smoke and other procarcinogenic substrates.

In one embodiment, this invention provides a diagnostic method for tobacco dependence risk and for cancers related to CYP2A6 substrates in an individual by analysing a DNA-containing bodily sample from the individual for the presence of a mutant allele of human cytochrome P450 enzyme CYP2A6. Preferably this method comprises genotype assaying the bodily sample, which may be genomic DNA isolated from peripheral leukocytes in the bodily sample. Alternatively the method comprises phenotype assaying the bodily sample, which may be a fluid, such as a blood sample or blood plasma. This invention also provides diagnostic kits for use in the analysis. The invention also provides a diagnostic method for tobacco dependence risk and for cancers related to human cytochrome P450 enzyme CYP2A6 substrates in an individual by administering a dose of a CYP2A6 substrate to the individual and determining in a bodily sample from the individual the level of said CYP2A6 substrate or a metabolite of said CYP2A6 substrate.

The invention specifically demonstrates that individuals who are carry CYP2A6 deficient alleles are less likely to become smokers and will smoke less cigarettes if tobacco-dependent. In addition, because CYP2A6 is known to activate procarcinogens, such as those found in tobacco-smoke, the diagnostic aspect of the invention will be useful for identifying the contribution of this polymorphic locus to the genetic risk of an individual for cancer.

If the result of the diagnostic assay is that the individual possesses wild-type CYP2A6 (i.e., the individual contains no mutant alleles of CYP2A6), the present diagnostic method and kit is predictive of an individual who: (i) has an increased risk of becoming a smoker, (ii) will smoke more if he/she becomes dependent, and/or (iii) may be at relatively higher risk for cancer due to both decreased smoke exposure and decreased enzyme mediated activation of procarcinogens. Once this individual is identified, he/she may be treated prophylactively with effective quantities of CYP2A6 inhibitors described in detail in copending International patent application Ser. No. PCT/CA97/00506 (filed Jul. 17, 1997) and U.S. provisional patent application Ser. No. 60/067,021 (filed on Dec. 1, 1997), which lead to other aspects of the present invention.

Thus, the invention also provides a smoking prevention composition or a smoking regulation composition comprising a CYP2A6 inhibitor, together with a carrier therefor, along with methods for preventing or regulating smoking by administering a CYP2A6 inhibitor to an individual. Likewise, this invention provides methods for cancer prevention or treatment or the regulation of the formation of carcinogens by administering a CYP2A6 inhibitor to an individual. Compositions containing a CYP2A6 inhibitor are also provided for use in these methods.

This invention provides methods for enhancing oral nicotine therapy, such as oral administration of nicotine bitartrate, by inhibiting nicotine metabolism through selective inhibition of CYP2A6, optionally with further selective inhibition of CYP2B6. Preferred inhibitors of CYP2A6 include coumarin, methoxsalen and tranylcypromine.

This method may be used to treat a condition requiring nicotine administration, preferably by administering a CYP2A6 inhibitor taken together with an oral formulation of nicotine, optionally also administering a CYP2B6 inhibitor. Preferred inhibitors of CYP2A6 include coumarin, methoxsalen and tranylcypromine.

The present inventors have surprisingly found that several natural products, are inhibitors of the enzyme CYP2A. Accordingly, the present invention provides a method of inhibiting CYP2A comprising administering an effective amount of a natural product or an extract of a natural product to an individual in need thereof, this method being useful in treating conditions requiring regulation of CYP2A activity. In one embodiment, the natural product is *Hypericum* or a *Hypericum* extract. In another embodiment, the natural product is *Cichorium intybus* or *Bougainvllra spectabillis* or an extract thereof.

This invention also provides a composition comprising an oral formulation of nicotine and a CYP2A6 inhibitor, optionally also containing a CYP2B6 inhibitor. Preferred inhibitors of CYP2A6 include coumarin, methoxsalen and tranylcypromine.

Other objects, features and advantages of the present invention will become apparent from the following detailed description. Aspects of this invention may be more fully deacribed in one or more of U.S. Provisional Patent Applications Nos. 60/067,20; 60/067,021; 60/084,847; and 60/107,392, which are each incorporated herein by reference in their entirety. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood with reference to the drawings in which:

FIG. 2A-2D show chemical structures of some representative CYP2A6 inhibitors;

DETAILED DESCRIPTION OF THE PREFERRED EMBODIMENTS

Figure 1:
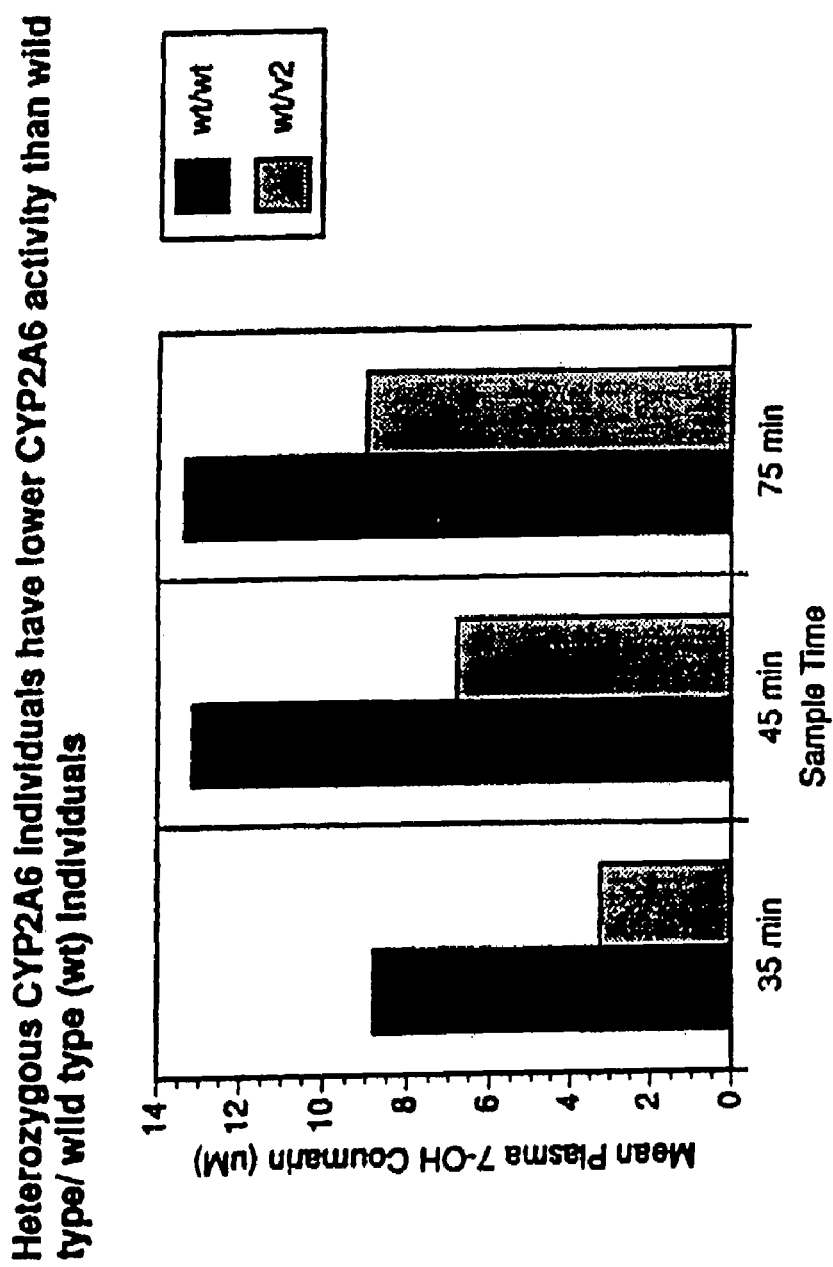
FIG. 1 this figure shows the application of a method to characterize CYP2A6 activity in human subjects by taking plasma samples at times as early as 35 minutes after administration of an oral dose of coumarin (100 mg in this example). Lower doses of coumarin may also be used and the data can also be expressed as a ratio of coumarin/7-OH coumarin. The test can also be performed using oral nicotine or another CYP2A6 substrate.

Broadly stated, the present invention relates to the diagnosis, prophylaxis and treatment of conditions requiring a reduction in the activity of a CYP2A enzyme. The term "CYP2A" as used herein means all isoforms of CYP2A including but not limited to CYP2A(CYP1), CYP2A6, CYP2A7, CYP2A12, CYP2A13 and CYP2A16. Preferably the enzyme is CYP2A6.

As described in copending International patent application Ser. No. PCT/CA97/00506, the contents of which are hereby incorporated by reference, inhibition of CYP2A6 (and optionally CYP2B6) inhibits the metabolism of nicotine. In particular, it was found that CYP2A6 is a major nicotine metabolizing enzyme in human livers and that by inhibiting CYP2A6 the metabolism of nicotine to continine in the liver is inhibited.

Diagnostic Methods

The present inventors have shown that individuals who carry CYP2A6 mutant alleles (i) have a decreased risk of becoming a smoker, (ii) will smoke less if he/she becomes dependent and/or (iii) may be at relatively lower risk for cancer due to both decreased smoke exposure and decreased CYP2A6-mediated activation of tobacco smoke and other procarcinogenic substrates.

Accordingly, the present invention provides a method for determining the risk of an individual becoming a smoker comprising determining the genotype or phenotype of a CYP2A allele in the individual wherein the presence of a mutant allele is predictive of a decreased risk of smoking. Preferably, the CYP2A enzyme is CYP2A6.

Tobacco smoke contains a number of tobacco-specific procarcinogen nitrosamines, for example the N-nitrosodiethylamine and 4-(methylnitrosamino)-1-(3-pyridyl)-1-butanone (NNK). These compounds are termed pro- or precarcinogens, as they are activated by the body. Specifically, these tobacco smoke procarcinogens can be activated by CYP2A6 (Crespi, et al., "Human cytochrome P450IIA3: cDNA sequence, role of the enzyme in the metabolic activation of promutagens, comparison to nitrosamine activation by human cytochrome P450IIE1," *Carcinogenesis* 11(8):1293-1300 (1990); Yamazaki, et al., "Cytochrome P450 2E1 and 2A6 enzymes as major catalysts for metabolic activation of N-nitrosodialkylamines and tobacco-related nitrosamines in human liver microsomes," *Carcinogenesis* 13(10):1789-94 (1992)). Therefore individuals who have CYP2A6 null alleles may also be less efficient at bioactivating tobacco smoke procarcinogens to carcinogens. This is of particular interest as ethnic variation in frequencies for CYP2A6 variant alleles exist (Nowak et al., 1998; Fernandez-Salguero P, et al., "A genetic polymorphism in coumarin 7-hydroxylation: sequence of the human CYP2A genes and identification of variant CYP2A6 alleles," *Am. J. Hum. Genet.*, 57(3):651-60 (1995); Yoloi and Kamataki, 1998) and may be related to the ethnic differences in lung cancer incidence and histology (Groeger et al., 1997). Thus, individuals carrying CYP2A6 defective alleles may have a decreased risk of developing tobacco-related cancers and other medical complications for three reasons. 1) They have a decreased risk of becoming a smoker. 2) If they do become tobacco-dependent, they smoke less than those without impaired nicotine metabolism resulting in lower exposures to tobacco-related procarcinogens (Law, et al., "The doseresponse relationship between cigarette consumption, biochemical markers and risk of lung cancer," *Br. J. Cancer* 75(11):1690-1693 (1997)). 3) They may activate fewer tobacco-related procarcincogens. These three factors suggest a significant reduction in tobacco-related cancers for carriers of a CYP2A6 defective allele(s).

Accordingly, the present invention provides a method for determining the risk of an individual for developing cancer comprising determining the genotype or phenotype of a CYP2A allele in the individual wherein the presence of a mutant allele is predictive of a decreased risk of developing cancer. Preferably, the CYP2A enzyme is CYP2A6.

The diagnostic aspect of this invention includes both phenotypic and genotypic methods for determining whether an individual has wild-type or mutant alleles for CYP2A6. The phenotypic assay may be performed by a metabolic study which is in effect an in vivo enzyme assay for CYP2A6 activity. This assay may be performed by administering a dose of a CYP2A6 substrate, for example nicotine or coumarin, and monitoring the physiological levels of the substrate and/or the product of enzymatic metabolism of the substrate in the individual at one or more time points during and subsequent to administration of the test dose. Typically, the levels will be measured in a biological fluid, such as blood, plasma, or urine, using well known assays for the particular components, examples of which are disclosed herein. An example of an in vivo phenotype and enzyme activity assay is provided in Example 3 below. This phenotypic assay can be used to classify individuals based on their normally expressed level of CYP2A6, which will correspond generally with the genotype of the individual as homozygous for fully active CYP2A6, heterozygous or homozygous for a lower activity allele, in decreasing order of nicotine metabolic rate.

The diagnostic aspect is also based on analysing a DNA-containing bodily sample from the individual for the presence of a mutant allele of human cytochrome P450 enzyme CYP2A6. As used throughout this specification, the term "mutant allele" is meant to encompass any allele having decreased or absent CYP2A6 activity, i.e., including null alleles. The presence of the mutant allele of CYP2A6 can be determined by conventional genotyping or phenotyping assays.

Many CYP2A6 alleles have been identified including, but not limited to, the wild-type allele (referred to throughout this specification as "CYP2A6*1"), and two defective or null mutant alleles ("CYP2A6*2" and "CYP2A6*3", respectively (see, Fernandez-Salguero, et al. 1995), the contents of which are hereby incorporated by reference). The CYP2A6*2 allele differs from the wild-type allele by a single point mutation which leads to a leucine to histidine amino acid change at codon 1609. In vitro and in vivo studies have demonstrated that this allele is a null allele. Mutations in the CYP2A6*3 allele occur in exons 3, 6, and 8. Very recently an additional CYP2A6 allele was identified which consists of an entire CYP2A6 gene deletion (Nunoya K et al., 1998 "A new deleted allele in the human cytochrome P450 2A6 (CYP2A6) gene found in individuals showing poor metabolic capacity to coumarin and (+)-cis-3,5-dimethyl-2-(3-pyridyl)thiazolidin-4-one hydrocholoride (SM-12502). Pharmacogenetics 1998, 8:239-249. Of course, additional mutant alleles which encode CYP2A6 enzymes with reduced activity may be found in individuals identified by the phenotypic and/or genotypic methods of this invention, and these individuals will also be expected to have lower risk of developing cancer and decreased risk of smoking.

The individual contemplated for the diagnostic methods of this invention (as well as the prophylactic and therapeutic methods described below) may be any type of mammal, but is preferably a primate, and more preferably a human.

Preferably, the bodily sample is a fluid such as blood or blood plasma. Alternatively, the bodily sample can be tissue. See, for example, Sambrook et al., *Molecular Cloning: A Laboratory Manual*, 2nd Edition, Cold Spring Harbor Laboratory Press (1989), the contents of which are hereby incorporated by reference, for discussion of general assay techniques useful with the diagnostic methods described herein.

With reference to FIG. 1, there is illustrated the result of CYP2A6 activity in a group (Group I) of individuals having heterozygous CYP2A6 activity (i.e., each individual in this group had a single mutant allele of CYP2A6 and a single active allele of CYP2A6) and a group of individuals (Group II) having wild type CYP2A6 activity (i.e. each individual in this group had two active alleles of CYP2A6). Blood plasma samples from each of the individuals in both groups were take post-administration of coumarin (100 mg) at 35 minutes, 45 minutes and 75 minutes. Coumarin 7-hydroxylation was used to assess the compliment activity of CYP2A6. The results of the phenotyping assay clearly show that the Group I individuals have a significantly lower CYP2A6 activity (less than half at 35 and 45 minutes) than the Group II individuals.

Alternatively, the subject is an individual having a CYP2A6 genotype associated with an active form of the enzyme. The CYP2A6 genotype of an individual and the existence of an active CYP2A6 enzyme in an individual may be determined using procedures using techniques described herein. For example, coumarin 7-hydroxylation has been used to measure CYP2A6 activity (see, Cholerton, et al. (1992) and Rautio, et al. (1992)).

The recognition by the present inventors that CYP2A6 is the major nicotine metabolizing enzyme in human livers suggests that the enzyme can be assayed in an individual to determine the individual's risk of developing tobacco dependence. Determination of CYP2A6 levels may also be used to select and monitor in an individual appropriate conventional nicotine replacement therapies such as the nicotine patch and nicotine gum. It is unlikely that conventional nicotine replacement therapies (e.g. nicotine gum, nicotine patch, spray, pulmonary inhalation or other forms) will have a high success outcome if an individual has high levels of CYP2A6, although such individuals may be good candidates for enhanced NRT according to the methods described herein. Conversely, if an individual has very low levels of CYP2A6, administering nicotine at high dosages will likely result in increased toxicity, and side effects. Furthermore, the co-administration of a CYP2A6 inhibitor with an existing NRT would be expected to decrease the kinetics of nicotine from that source and to enhance the efficacy of the NRT (discussed below under Therapeutic Methods).

Prophylactic and Therapeutic Methods

As mentioned previously, the present invention relates to methods for the prophylaxis and treatment of conditions requiring a reduction in the activity of a CYP2A enzyme. In particular, the prophylactic/therapeutic aspect of the present invention relates to treatment and prevention of smoking, in vivo carcinogen formation and cancer in an individual. Each of this involves administration to an individual of a CYP2A inhibitor, preferably a CYP2A6 inhibitor.

In one aspect, the present invention provides a method of preventing, treating or regulating smoking in an individual comprising administering an effective amount of one or more substances selected from the group consisting of (i) substances which inhibit CYP2A activity; (ii) substances which inhibit transcription, translation of the gene encoding CYP2A, or both; (iii) substances which delete all or a portion of the gene encoding CYP2A. Preferably, the CYP2A is CYP2A6.

As used throughout this specification, the terms "smoking prevention" and "preventing smoking", as used throughout this specification, are intended to mean that the likelihood of the onset of smoking (i.e., the progression from a cigarette to regular smoking) in a current non-smoking individual (i.e., a person who has never smoked or is a ex-smoker) and the return to smoking of a previous smoker (i.e. relapse prevention) is substantially mitigated.

The terms "smoking regulation" and "regulating smoking", as used throughout this specification, are intended to mean that the amount smoked by a current smoking individual is reduced or, at least, fails to increase.

The terms "smoking treatment" or "treatment of smoking" means the stopping of all smoking or the reduction in amount of smoking as reflected in less use of tobacco products, a decrease in pattern of use or a decrease in tobacco smoke exposure. The measure of tobacco smoke exposure can be measured by analyzing breath carbon monoxide.

In another aspect, the present invention provides a method of regulating the formulation of a carcinogen in an individual comprising administering an effective amount of one or more substances selected from the group consisting of (i) substances which inhibit CYP2A activity; (ii) substances which inhibit transcription, translation of the gene encoding CYP2A, or both; (iii) substances which delete all or a portion of the gene encoding CYP2A. Preferably, the CYP2A is CYP2A6.

The terms "carcinogen formation regulation" and "regulating formation of a carcinogen", as used throughout this specification, are intended to mean that the occurrence of carcinogen formation in an individual is reduced. This may be achieved, for example, by using CYP2A6 inhibition to inhibit activation of procarcinogens present in the individual. As used throughout this specification, the term "procarcinogen" is meant to encompass any substance which is at least one of procytotoxic, promutagenic and progenotoxic ("pro" means the metabolite is more active that the parent compound).

In a further aspect, the present invention provides a method of preventing cancer in an individual comprising administering an effective amount of one or more substances selected from the group consisting of (i) substances which inhibit CYP2A activity; (ii) substances which inhibit transcription, translation of the gene encoding CYP2A, or both; (iii) substances which delete all or a portion of the gene encoding CYP2A. Preferably, the CYP2A is CYP2A6.

The terms "cancer prevention" and "preventing cancer", as used throughout this specification, are intended to mean that the likelihood of the onset of cancer in a current cancer-free individual (i.e., a person who has never had cancer or whose cancer is in remission) is substantially mitigated.

The terms "inhibitor" and "inhibition", in the context of the present invention, are intended to have a broad meaning and encompass substances which directly or indirectly (e.g., via reactive intermediates, metabolites and the like) act on CYP2A to inhibit or otherwise regulate the ability of CYP2A to catalyze metabolism of a substrate. Other substances which act indirectly on CYP2A include those substances which inhibit transcription and/or translation of the gene encoding CYP2A. In particular, the terms "CYP2A6 inhibition" and "CYP2A6 inhibitor" are intended to have a broad meaning and encompass any substance which: (i) inhibits CYP2A6 activity; (ii) inhibits transcription and/or translation of the gene encoding CYP2A6; or (iii) deletes or removes the gene encoding CYP2A6. Particularly preferred substances are those which alter the kinetics for metabolism of nicotine to cotinine, alter smoking behavior, alter the likelihood of addiction to smoking in a population of non-smokers, or alter the kinetics of formation for carcinogens whose formation from procarcinogens is catalyzed by CYP2A, and more preferably exhibit the biological altering effect without producing other biological effects at significant levels.

A substance will "selectively" inhibit CYP2A activity when the substance can alter the kinetics for metabolism of nicotine to cotinine, alter smoking behavior, alter the likelihood of addiction to smoking in a population of non-smokers, or alter the kinetics of formation for carcinogens whose formation from procarcinogens is catalyzed by CYP2A generally at a dosage level which is lower than the dosage of the substance which is effective for production of another biological effect. For example, it is shown below that administration of methoxsalen acted to increase plasma levels of nicotine and to reduce desire to smoke in dependent smokers at levels that were one-fourth the therapeutic dose for treatment of psoriasis by methoxsalen.

The term "effective amount" as used herein means an amount effective and at doses and for periods of time necessary to achieve the desired results; this may mean limiting doses where the desired result is selective inhibition and selectivity is achieved through differential inhibition of CYP2A. Preferably, the substances inhibit CYP2A6.

CYP2A6 Inhibitors

As hereinbefore mentioned, in one of its aspects, the present invention relates to a method of regulating nicotine metabolism to cotinine in an individual comprising selectively inhibiting CYP2A6. Inhibition of CYP2A6 may be achieved using one or more of the following (i) substances which inhibit CYP2A6 activity; or (ii) substances which inhibit transcription and/or translation of the gene encoding CYP2A6.

Substances which inhibit CYP2A6 activity include substances which specifically bind to CYP2A6 and thereby inhibit its activity. Examples of such substances include antibodies which are specific for CYP2A6 including for example, the monoclonal antibody described by Pearce R, et al. ("Species differences and interindividual variation in liver microsomal cytochrome P450 2A enzymes: effects on coumarin, dicumarol, and testosterene oxidation," *Arch. Biochem. Biophys.*, 298(1): 211-225 (1992)), and commercially available antibodies such as MAB2A6 and monoclonal CYP2A6, sold by Gentest Corporation, Woburn, Mass., U.S.A.; XenoTech 2A6 sold by XenoTech LLC, Kansas City, Kans., U.S.A and polyclonal CYP2A6 sold by Research Diagnostics, Inc, Flanders, N.J., U.S.A.

Preferred inhibitors of CYP2A6 include methoxsalen, psoralen, tranylcypromine, pilocarpine, coumarin, chromone, esculetin, phenelzine, paroxetine, selegiline and pargyline.

Substances which inhibit CYP2A6 activity also include substances having a lactone structure with a carbonyl oxygen. Non-limiting examples of such substances include coumarin (The Merck Index, Eleventh Edition Budavari, S., ed. Merck & Co. Inc., 1989, No. 2563), furanocoumarin, methoxsalen (The Merck Index, No. 5911), imperatorin (The Merck Index, No. 4839), psoralen (The Merck Index, No. 7944), a-naphthoflavone, isopimpinellin, β-naphthoflavone, bergapten (The Merck Index, No. 1173), sphondin, coumatetralyl (racumin), and (+)-cis-3,5-dimethyl-2-(3-pyridyl)-thiazolidim-4-one (SM-12502) (Nunoya, et al., *J Pharmacol. Exp. Ther.*, 277(2):768-74 (1996)). Other substances which inhibit CYP2A6 and can be used in the methods and compositions of the invention include narin-genin and related flavones, diethyldithiocarbamate, nicotine (useful primarily in the screening methods of the invention), N-nitrosodialkylamine (e.g. N-nitrosodiethylamine (The Merck Index, No. 6557), N-nitrosodimethylamine (The Merck Index, No. 6558)), nitropyrene, menadione (The Merck Index, No. 5714), imidazole antimycotics, miconazole (The Merck Index, No. 6101), clotrimazole (The Merck Index, No. 2412), pilocarpine (The Merck Index, No. 7395), hexamethylphosphoramide, 4-methylnitrosamine-3-pyridyl-1-butanol, aflatoxin B (The Merck Index, No. 168), tranylcypromine (the Merck Index, No. 9491), including cis, trans, (+) and (−) isomers, trioxsalen, alaproclate, phenelzine, pargyline, paroxitine, selegiline, amphetamine, bupropion, buspirone, citalopram, desmethylcitalopram, doxeprine, fluoxetin, naltrexone, norfluoxetine, nortriptyline, sertraline, trazodone, viaqualine, zimelidine, chromone, bergapten and narigenin. All of the substances that inhibit CYP2A6 activity include racemic mixtures of the compounds as well as the cis, trans, (+) and (−) isomers. See FIGS. 2A to 2D for the chemical structures of these and other non-limiting representative inhibitors. Selective and non-selective monoamine oxidase inhibitors (e.g., alaproclate, phenelzine, deprenyl, pargyline, selegiline and the like) are particularly preferred. Various isomers of the above compounds which can be shown to inhibit CYP2A6 as described below are within the contemplation of this invention.

Derivatives and analogs of these substances may also be used in the methods and compositions of the invention. Derivatives and analogs include compounds that are structurally similar to the compounds described herein and can bind to the CYP2A6 active site. For example, derivatives of tranylcypromine, coumarin and methoxsalen include pharmaceutically acceptable salts, esters and complexes of tranylcypromine, coumarin and methoxsalen including potassium and sodium salts, and amino acid, carbohydrate and fatty acid complexes. By way of example, suitable analogs of coumarin may be selected based upon their functional similarity to coumarin, including the ability to inhibit the metabolism of nicotine to cotinine by CYP2A6. Examples of functional analogs of coumarin include 7-methoxycoumarin, 7-methylcoumarin, and 7-ethoxycoumarin and all structures shown in FIGS. 2A, 2B, 2C. Analogs of coumarin may also be selected based upon their three dimensional structural similarity to coumarin—i.e., the lactone/carbonyl structure.

The present inventors have surprisingly found that natural products and extracts of natural products inhibit CYP2A6 activity in both human liver microsomes and pure full-length human cDNA expressed cytochromes. Accordingly, CYP2A6 inhibitors of the present invention include natural products or extracts of a natural product capable of inhibiting CYP2A6, such as *Hypericum* or a *Hypericum* extract or *Cichorium intybus* or *Bougainvllra spetabillis* or an extract thereof.

The term "*Hypericum*" as used herein as synonymous with *Hypericum perforatum*, St. John's Wort, Goatweed and Klamath Wee. The phrase "*Hypericum* or an extract of *Hypericum*" as used herein includes the whole plant *Hypericum perforatum* or a derivative, extract, isolate or purified component thereof that can inhibit CYP2A activity. This includes natural components of the plant and synthetic analogues. A preferred extract of *Hypericum* is a methanol extract.

Derivatives of *Hypericum* which may be used in the methods and compositions of the invention include hypericin, pseudohypericin, quercetin, hyperoside, quercitrin, isoquercitrin, rutin, campherol, luteolin, 13-II8-biopigenin, 1,3, 6,7-tetrahydroxyxanthone, procyanidines, hyperforin, ethereal oil, phenol carbonic acids (e.g. chlorogenic acid), xanthone, phenylpropanes, flavonol derivatives, biflavones, proanthocyanidins, xanthones, phloroglucinols, naphthodianthrones and essential oil constitutes. Also included are the pharmaceutically acceptable salts, esters and complexes of the derivatives including potassium and sodium salts, and amino acid, carbohydrate and fatty acid complexes. Suitable derivatives of *Hypericum* may be selected based upon their ability to inhibit CYP2A with greater than 50% inhibition, and/or a Ki less than 300 μM.

The phrase "*Cichorium intybus* or *Bougainvllra spectabillis* or an extract thereof" as used herein includes the whole plants *Cichorium intybus* or *Bougainvllra specabillis* or a derivative, extract, isolate or a purified component thereof that can inhibit CYP2A activity. This includes natural components of the plants as well as synthetic analogues. A preferred extract from *Cichorium intybus* or *Bougainvllra spectabillis* is esculetin, esculin or esculin monohydrate.

Figure 20:
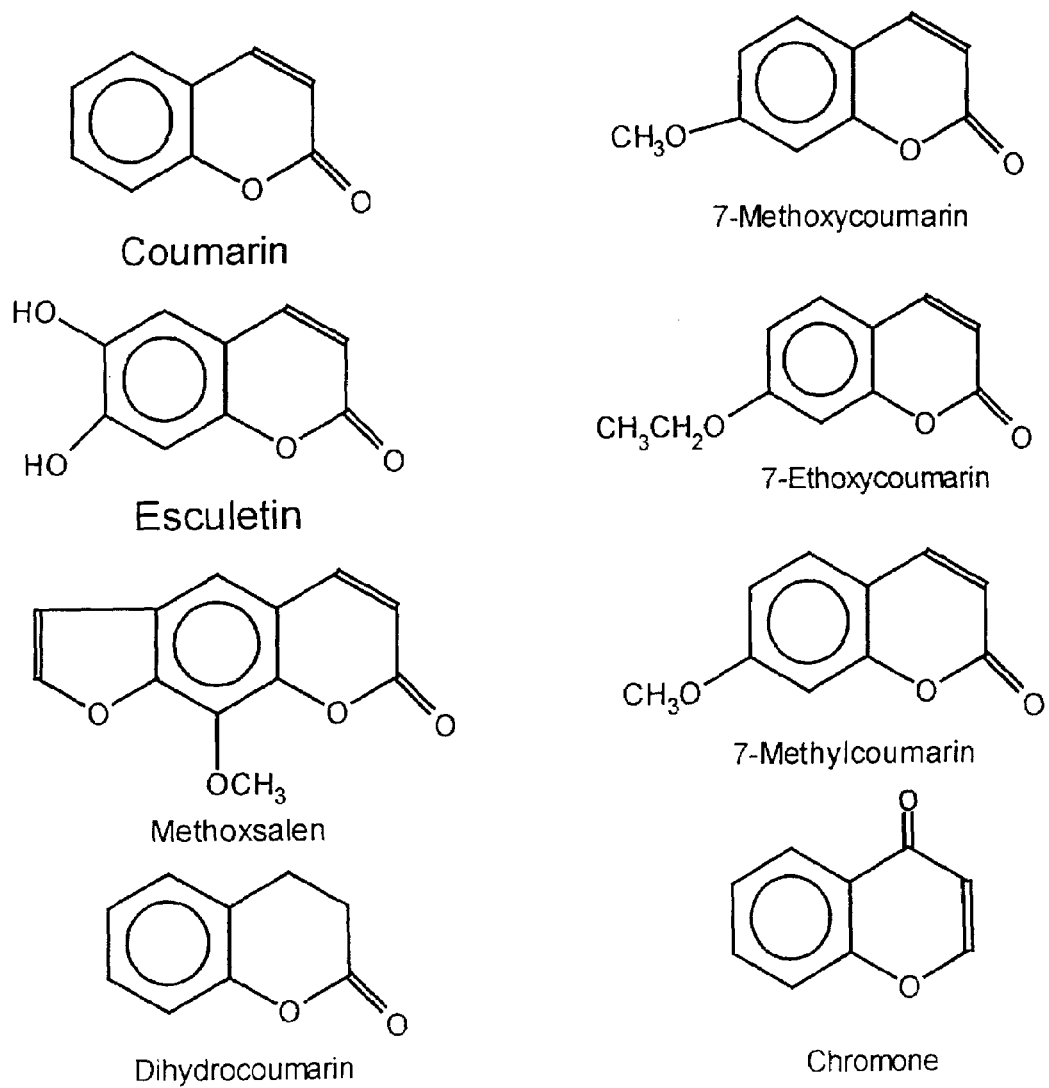
FIG. 20 shows the chemical structure of various compounds found in natural products.

Other extracts of natural products that may be useful in the present invention are shown in FIG. 20, and in U.S. provisional application Ser. No. 60/084,847, which is incorporated herein by reference.

The above lists of substances which inhibit CYP2A6 are provided by way of example only and should not be seen as limiting the scope of this invention. Additional substances which inhibit CYP2A6 activity may be identified using the screening methods described herein.

Substances which inhibit transcription and/or translation of the gene encoding CYP2A6 include a nucleic acid sequence encoding the CYP2A6 gene (GenBank Accession No. HSU22027) or parts thereof (e.g., the region which is about 20 nucleotides on either side of nucleotide 790 (ATG), and the splice sites 1237, 2115, 2499, 3207, 4257, 4873, 5577 and 6308), inverted relative to their normal orientation for transcription—i.e., antisense CYP2A6 nucleic acid molecules. Such antisense nucleic acid molecules may be chemically synthesized using naturally occurring nucleotides or variously modified nucleotides designed to increase the biological stability of the molecules or to increase the physical stability of the duplex formed with CYP2A6 mRNA or the CYP2A6 gene. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

A nucleic acid molecule containing the antisense sequences may be introduced into cells in a subject using conventional techniques, such as transformation, transfection, infection, and physical techniques such as electroporation or microinjection. Chemical methods such as coprecipitation and incorporation of DNA into liposomes may also be used to deliver antisense sequences. The molecules may also be delivered in the form of an aerosol or by lavage. Suitable vectors or cloning vehicles for transferring the nucleic acid molecules are known in the art. Examples of suitable vectors include retroviral vectors, adenoviral vectors, and DNA virus vectors.

The ability of a substance to selectively inhibit CYP2A6 and thus regulate nicotine metabolism to cotinine may be confirmed using the methods described herein for screening for an inhibitor.

Figure 2A:
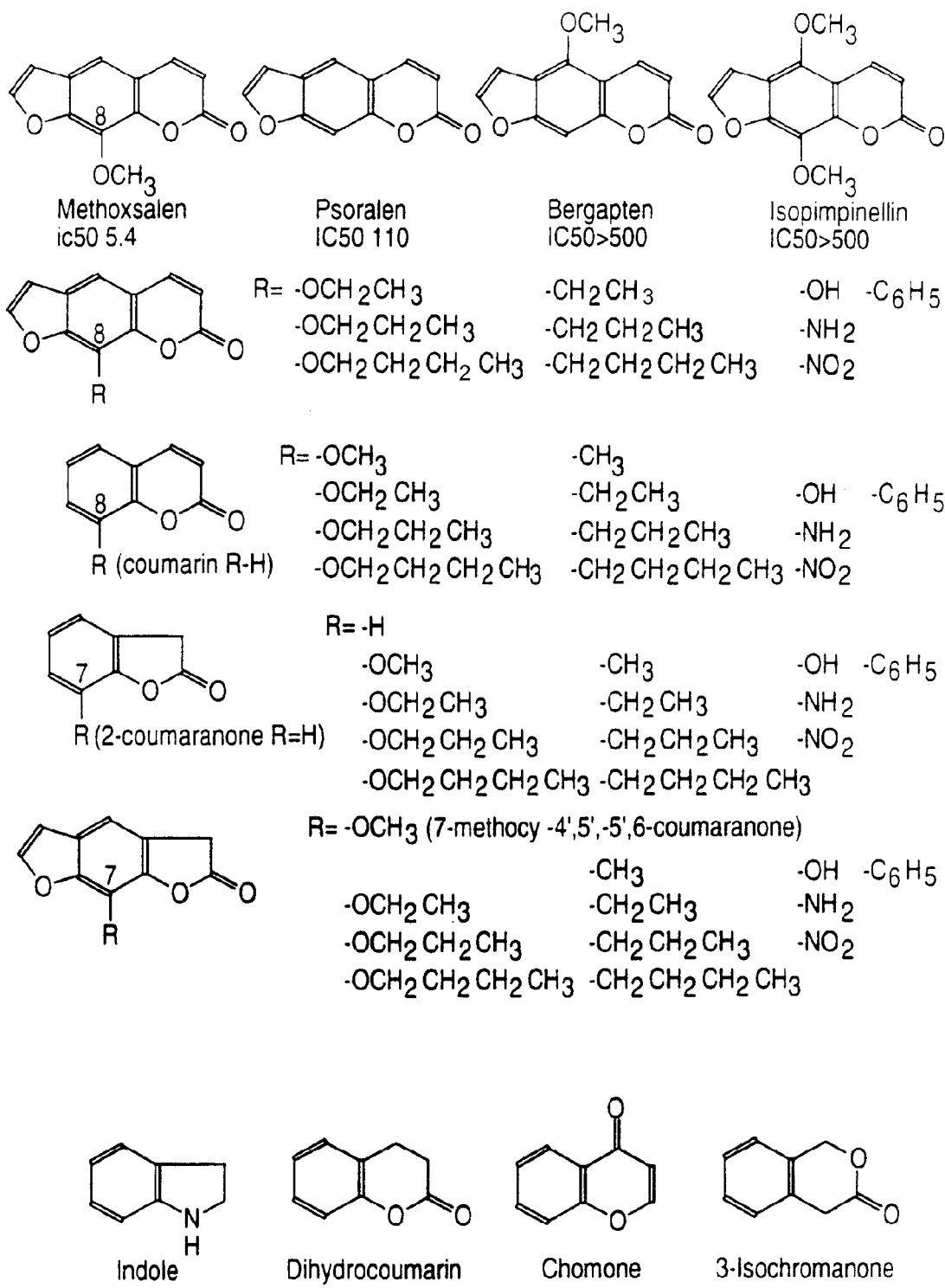
Figure 2B:
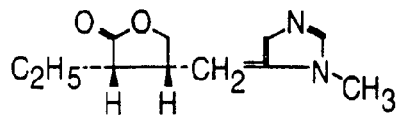
Figure 2B:
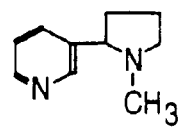
Figure 2B:
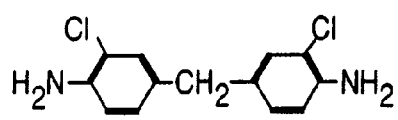
Figure 2B:
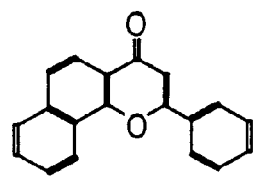
Figure 2B:
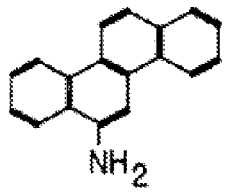
Figure 2B:
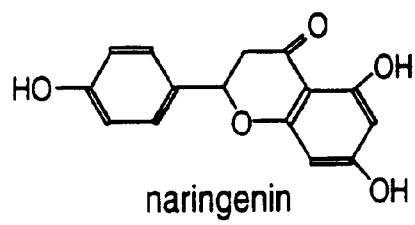
Figure 2B:
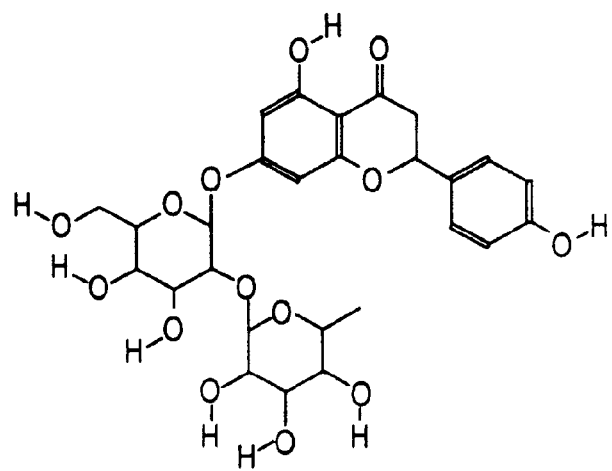
Figure 2C:
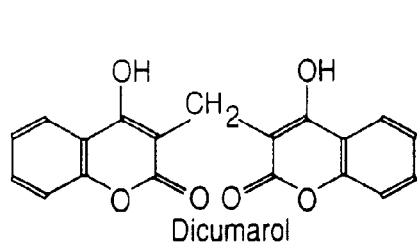
Figure 2C:
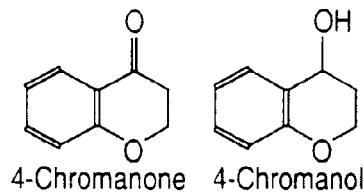
Figure 2C:
Figure 2C:
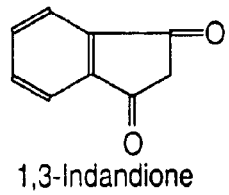
Figure 2C:
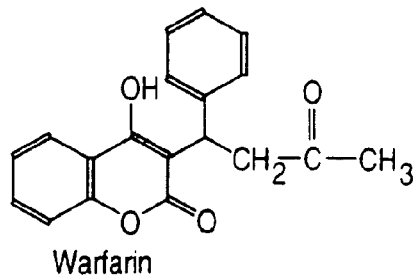
Figure 2C:
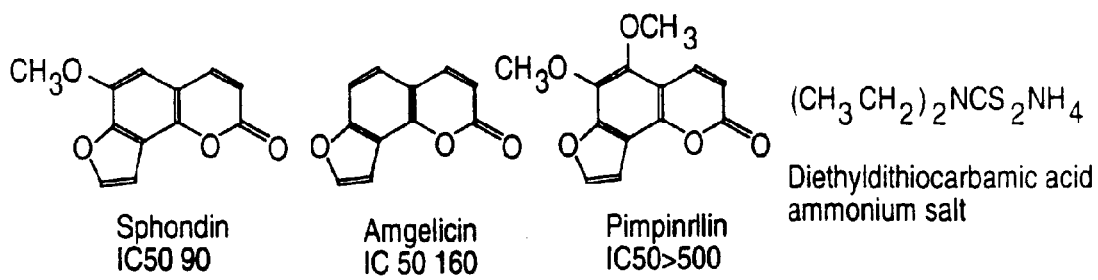
Figure 2C:
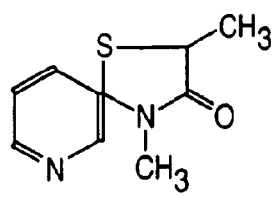

In one embodiment of the invention, the CYP2A6 inhibitor is at least one member selected from the group comprising coumarin, methoxsalen, tranylcypromine, derivatives thereof and analogs thereof (see FIG. 2A). Initial in vitro screening and clinical studies have identified that methoxsalen is a potent inhibitor of CYP2A6.

CYP2A6 may also be selectively inhibited in the method of the invention by interfering with the transcription of the gene encoding CYP2A6 using gene transfer methods such as targeted gene mutagenesis using allelic replacement, insertional inactivation, or deletion formation. For example, allelic gene exchange using non-replicating or conditionally-replicating plasmids has been used widely for the mutagenesis of eukaryotes. Allelic exchange can be used to create a deletion of the CYP2A6 gene. Exemplary methods of making the alterations set forth above are disclosed by Sambrook, et al. (1989).

CYP2B6 Inhibitors

CYP2B6 inhibitors may also be used in combination with inhibitors of CYP2A6 to provide an enhanced inhibitory effect. Inhibitors of CYP2B6 include one or more of the following (i) substances which inhibit CYP2B6 activity; or (ii) substances which inhibit transcription and/or translation of the gene encoding CYP2B6. CYP2B6 inhibitors may also be used alone to inhibit nicotine metabolism in an individual.

Substances which inhibit CYP2B6 activity include substances which specifically bind to CYP2B6 and thereby inhibit its activity. Examples of such substances include antibodies which are specific for CYP2B6 including for example, commercially available antibodies such as anti-CYP2B6 sold by Gentest Corporation, Woburn, Mass., U.S.A.

Substances which inhibit CYP2B6 activity also include substances selected from phenylethyl amines, diphenylbarbiturates, diethyl substituted barbiturates and hydantoins. In particular, diphenhydramine and its derivatives, including orphenadrine (The Merck Index, No. 6831), and derivatives or analogs of orphenadrine, and other antihistamines, anticholinergic substances such as cholines and analogs and derivatives thereof may be used as CYP2B6 inhibitors in various embodiments of the methods and compositions of the invention. Antibodies, such as polyclonal CYP2B1/2, polyclonal CYP2B1 and polyclonal CYP2B6 sold by Gentest Corporation, Woburn, Mass., U.S.A., also bind specifically to CYP2B6 such that they also inhibit the activity of CYP2B6.

Derivatives of orphenadrine which may be used in the methods and compositions of the invention include pharmaceutically acceptable salts, esters and complexes of orphenadrine including potassium and sodium salts, and amino acid, carbohydrate and fatty acid complexes. In one embodiment, suitable analogs of orphenadrine may be selected based upon their functional similarity to orphenadrine, including the ability to inhibit CYP2B6. Analogs of orphenadrine may also be selected based upon their three dimensional structural similarity to orphenadrine.

Substances which inhibit transcription and/or translation of the gene encoding CYP2B6 include a nucleic acid sequence encoding the CYP2B6 gene (see FIG. 2B, GenBank Accession No. HSP452B6 for the mRNA sequence of CYP2B6), or parts thereof (e.g., the region which is on either side of nucleotide 9 (ATG), and the sites 111, 274, 424, 585, 762, 904, 1092, and 1234 nt), inverted relative to their normal orientation for transcription—i.e., antisense CYP2B6 nucleic acid molecules. Such antisense nucleic acid molecules may be produced and introduced into cells using conventional procedures as described herein.

CYP2B6 may also be selectively inhibited in a method of the invention by interfering with the transcription of the gene encoding CYP2B6 using conventional gene transfer methods as discussed herein.

In preferred embodiments of the invention the CYP2B6 inhibitor employed is orphenadrine and derivatives or analogs of orphenadrine.

An inhibitor of CYP2A6 or CYP2B6 may be targeted to the enzyme using antibodies specific to an epitope of the enzyme. For example, bispecific antibodies may be used to target an inhibitor. The bispecific antibodies contain a variable region of an antibody specific for at least one epitope of CYP2A6 or CYP2B6, and a variable region of a second antibody which is capable of binding to an inhibitor. The bispecific antibodies may be prepared by forming hybrid hybridomas, using procedures known in the art such as those disclosed in Staerz, et al. ("Hybrid hybridoma producing a bispecific monoclonal antibody that can focus effector T-cell activity," *Proc. Natl. Acad. Sci. USA,* 83(5):1453-7 (1986)) and Staerz, et al. (Immunology Today, 7:241 (1986)). Bispecific antibodies may also be constructed by chemical means using conventional procedures such as those described by Staerz, et al. ("Hybrid antibodies can target sites for a attack by T cells," *Nature,* 314(6012):628-31 (1985)) and Perez, et al. ("Specific targeting of cytotoxic T cells by anti-T3 linked to anti-target cell antibody," *Nature,* 316(6026):354-6 (1985)), or by expression of recombinant immunoglobulin gene constructs.

Nicotine Replacement Therapy

An oral nicotine replacement therapy containing nicotine alone would be ineffective due to the extensive metabolism of nicotine in the liver which significantly decreases the systemic availability of the nicotine. However, administering the nicotine with a CYP2A inhibitor would increase the bioavailability and the effectiveness of the oral nicotine therapy.

The present invention also includes a nicotine replacement therapy comprising contemporaneously administering to an individual in need thereof (a) oral nicotine and (b) one or more substances selected from the group consisting of (i) substances which inhibit CYP2A activity; (ii) substances which inhibit transcription, translation of the gene encoding CYP2A, or both; (iii) substances which delete all or a portion of the gene encoding CYP2A.

Preferably, the inhibitor is an inhibitor of CYP2A6 such as methoxsalen or tranylcypromine.

As used herein, "contemporaneous administration" of two substances to an individual means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens are routine for one skilled in the art, in view of the details provided herein on the biological activities of CYP2A6 substrates and inhibitors. In particular embodiments, two substances will be administered substantially simultaneously, i.e., within minutes of each other, or in a single composition that contains both substances. On the other hand, a CYP2A6 inhibitor which acts by deleting or removing the gene encoding CYP2A6 could be administered months or even years before administration of nicotine or a procarcinogen that would otherwise be converted to a carcinogen by CYP2A6, and the effects due to the two administrations may still be contemporaneous.

Screening for Inhibitors

In addition to the CYP2A inhibitors listed above, substances which may be used in the methods of this invention include other substances that alter the kinetics for metabolism of nicotine to cotinine, alter smoking behavior, alter the likelihood of addiction to smoking in a population of non-smokers, alter the kinetics of formation for carcinogens whose formation from procarcinogens is catalyzed by CYP2A. All of these substances have in common an ability to reduce the activity of CYP2A enzymes in an individual. The present disclosure therefore provides a method of screening for a substance that inhibits a CYP2A enzyme in an individual comprising assaying for a substance which selectively (i) inhibits CYP2A6 activity, (ii) inhibits transcription and/or translation of the gene encoding CYP2A6, or (iii) deletes or removes the gene encoding CYP2A6.

The inhibitory activity of a particular substance identified herein or an analog or derivative thereof may be confirmed by testing in experimental model systems and in clinical studies, for example as outlined below and exemplified in the Examples herein. Furthermore, specificity or selectivity of a substance listed above or a substance newly identified by screening as described herein may be determined or confirmed as described hereinbelow. While no particular test is mandated by this invention, the usefulness of a particular substance (e.g., a substance not specifically listed hereinabove or referred to in FIG. 2A-2D) as a CYP2A6 inhibitor may be readily determining by testing the substance as follows.

In vitro Inhibition

An initial screen to select candidate inhibitors for use in the methods according to this invention comprises:

(a) reacting, in the presence of a test substance, a substrate of CYP2A6 with a source of CYP2A6 under conditions such that CYP2A6 is capable of converting the substrate into a reaction product;

(b) assaying for reaction product, unreacted substrate or unreacted CYP2A6;

(c) comparing the results of such assay to controls in the absence of the substance to determine if the test substance inhibits CYP2A6 and thereby is capable of inhibiting CYP2A enzymes.

Substrates of CYP2A6 which may be used in the in vitro test for identification of substances for use in methods of the invention, as well as in the in vivo tests below, include nicotine, coumarin, analogs thereof and derivatives thereof. The corresponding reaction products for nicotine and coumarin are cotinine and 7-hydroxycoumarin, respectively.

CYP2A6 used in the method of the invention may be obtained from natural, recombinant, or commercial sources. For example CYP2A6 may be obtained by recombinant methods such as those described by Nesnow S, et al. ("N-nitrosodiethylamine and 4-(methylnitrosamino)-1-(3-pyridyl)-1-butanone induced morphological transformation of C3H/10T1/2CL8 cells expressing human cytochrome P450 2A6," *Mutation Research,* 324:93-102 (1994)). Cells or liver microsomes expressing CYP2A6 may also be used in the method.

Conditions which permit the formation of a reaction product may be selected having regard to factors such as the nature and amounts of the test substance and the substrate. The results using the substrates in the presence and absence of the test substance may be compared to results using methoxsalen or tranylcypromine as controls which show positive inhibition tests.

The reaction product, unreacted substrate, or unreacted CYP2A6; may be isolated by conventional isolation techniques, for example, salting out, chromatography, electrophoresis, gel filtration, fractionation, absorption, polyacrylamide gel electrophoresis, agglutination, or combinations thereof.

To facilitate the assay of the reaction product, unreacted substrate, or unreacted CYP2A6; antibody against the reaction product or the substance, or a labeled CYP2A6 or substrate, or a labeled substance may be utilized. Antibodies, CYP2A6, substrate, or the substance may be labeled with a detectable marker such as a radioactive label, antigens that are recognized by a specific labeled antibody, fluorescent compounds, enzymes, antibodies specific for a labeled antigen, and chemiluminescent compounds.

The substrate used in the method of the invention may be insolubilized. For example, it may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized CYP2A6, substrate, or substance may be prepared by reacting the material with a suitable insoluble carrier using known chemical or physical methods, for example, cyanogen bromide coupling.

In vivo Inhibition

Substances which pass the above-mentioned in vitro screening test are then preferably subjected to an in vivo test to confirm their suitability for use in the methods of this invention. A suitable in vivo test method comprises the steps of:

(a) administering a subtherapeutic dose of nicotine (e.g., 1.0, 2.0 or 4.0 mg expressed as the base) in an oral formulation to an individual, together with the test substance;

(b) collecting pre-nicotine and post-nicotine plasma samples from the individual (e.g., 30, 60 and 90 minutes after (a));

(c) determining the plasma nicotine concentration using a conventional analytical technique (e.g., HPLC, gas chromatography and the like), and (d) comparing the plasma nicotine concentration to a control (i.e., nicotine given without test substance) to assess whether the test substance results in a statistically significant increase in the plasma nicotine concentration at one or more time points, more preferably the later time points.

Genetic Level Effectors

Analogous methods may be used for screening for a substance that regulates nicotine metabolism to cotinine in an individual by inhibiting transcription and/or translation of the gene encoding CYP2A6. A screening method for such substances comprises the steps of:

(a) culturing a host cell comprising a nucleic acid molecule containing a nucleic acid sequence encoding CYP2A6 and the necessary elements for the transcription or translation of the nucleic acid sequence, and optionally a reporter gene, in the presence of a test substance; and (b) comparing the level of expression of CYP2A6, or the expression of the protein encoded by the reporter gene with a control cell transfected with a nucleic acid molecule in the absence of the test substance.

A host cell for use in the method of the invention may be prepared by transfecting a suitable host with a nucleic acid molecule comprising a nucleic acid sequence encoding CYP2A6. A nucleic acid sequence encoding CYP2A6 may be constructed having regard to the sequence of the CYP2A6 gene (see the sequence under Genbank Accession number HUS22027, incorporated herein by reference) following procedures known in the art. Suitable transcription and translation elements may be derived from a variety of sources, including bacterial, fungal, viral, mammalian, or insect genes. Selection of appropriate transcription and translation elements is dependent on the host cell chosen, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be supplied by the native CYP2A6 gene and/or its flanking sequences.

Examples of reporter genes are genes encoding a protein such as β-galactosidase, chloramphenicol acetyltransferase, firefly luciferase, or an immunoglobulin or portion thereof such as the Fc portion of an immunoglobulin, preferably IgG. Transcription of the reporter gene is monitored by changes in the concentration of the reporter protein such as β-galactosidase, chloramphenicol acetyltransferase, or firefly luciferase. This makes it possible to visualize and assay for expression of CYP2A6 and in particular to determine the effect of a substance on expression of CYP2A6.

Suitable host cells include a wide variety of prokaryotic and eukaryotic host cells, including bacterial, mammalian, yeast or other fungi, viral, plant, or insect cells.

Protocols for the transfection of host cells are well known in the art (see, Sambrook, et al. (1989)). By way of example, Nanji M, et al. ("Expression in a baculovirus system of a cDNA encoding human CYP2A6," *Biochem. Soc. Trans.*, 22 (1994)) describe the expression of a cDNA encoding human CYP2A6 in a baculovirus system; Nesnow, S., et al. (1994) and Tiano H F, et al. ("Retroviral mediated expression of human cytochrome P450 2A6 in C3H/10T1/2 cells confers transformability by 4-(methylnitrosamino)-1-(3-pyridyl)-1-butanone (NNK)," *Carcinogensis*, 14:1421-7 (1993)) describe the expression of CYP2A6 from a retroviral vector in transformable C3H/10T1/2 mouse embryo fibroblasts; and Salonpaa P, et al. ("Retrovirus-mediated stable expression of human CYP2A6 in mammalian cells," *Eur. J Pharmacol.*, 248:95-102 (1993)) describe the preparation of amphotropic recombinant retroviruses containing CYP2A6 using LXSN vector and PA317 packaging cells.

Host cells which are commercially available may also be used in the method of the invention. For example, the h2A3 (now known as h2A6) and h2B6 cell lines available from Gentest Corporation are suitable for the screening methods of the invention.

Substances which pass the in vitro screening test for alteration of expression of CYP2A6 preferably are then subjected to an in vivo test to confirm their suitability for use in the methods of this invention, by analogy to the in vivo test for inhibitors of CYP2A enzyme activity.

The above mentioned methods may be used to identify negative regulators of nicotine metabolism to cotinine in brain and liver thereby affecting conditions requiring regulation of nicotine metabolism. Further confirmation of the suitability of the substances, and/or demonstration of the selectivity of the effects, may be achieved by population studies of the effects of the substances on the kinetics for metabolism of nicotine to cotinine, on smoking behavior, on the likelihood of addiction to smoking in a population of non-smokers, and/or on the kinetics of formation for carcinogens whose formation from procarcinogens is catalyzed by CYP2A. Such studies are a routine matter for the skilled clinician in view of the guidance provided herein and the exemplary studies described in the Examples below.

Compositions

Substances which inhibit CYP activity described in detail herein, or substances identified using the methods of the invention may be incorporated into pharmaceutical compositions. Therefore the invention provides a pharmaceutical composition for use in treating a condition requiring a reduction in the activity of a CYP2A enzyme comprising an effective amount of one or more substances which selectively inhibit CYP2A6, and a pharmaceutically acceptable carrier, diluent, or excipient. In one of its aspects, the invention provides a pharmaceutical composition for use in smoking prevention, smoking treatment, smoking regulation, regulating carcinogen formation, cancer prevention and/or cancer treatment. A method of treatment using such a composition is also provided. Further, the treatment methods and compositions of the invention may also be used together with other active compounds, including such other active compounds which are susceptible to CYP2A6-mediated metabolism leading to an inhibition or reduction in effectiveness of the other active compound.

Conditions requiring regulation of nicotine metabolism to cotinine include nicotine use disorders—i.e., dependent and non-dependent tobacco use, and nicotine-induced disorders—i.e., withdrawal. The conditions may develop with the use of all forms of tobacco (e.g., cigarettes, chewing tobacco, snuff, pipes, and cigars) and with prescription medications (e.g. nicotine gum, nicotine patch, spray, pulmonary inhalation or other forms). In particular, the pharmaceutical compositions and treatment methods of the invention may be used to diminish a subjects desire to smoke and thereby alter smoking behaviour. The pharmaceutical compositions and treatment methods of the invention may also be used together with other centrally active pharmaceutical compositions that modify smoking behaviour (e.g. bupropion (a.k.a. Wellbutrin®) in its various formulations), to decrease the dose of the centrally active composition or to increase its effectiveness in the treatment of tobacco dependence.

The compositions and treatment methods of the present invention by regulating nicotine metabolism in an individual are highly effective. The methods and compositions maintain the behavioural components of smoking and modify them by reducing nicotine metabolism to cotinine. An individual with reduced nicotine metabolism following administration of a composition of the present invention, will alter smoking behaviour and smoke exposure because of modification of nicotine requirements. The methods and compositions of the invention show patterns of reduction, more sustained abstinence, and lower tobacco smoke exposure than obtained with prior art methods in particular those using nicotine deprivation.

The behavioural component of smoking is particularly important in some groups of individuals, and thus the methods and compositions of the invention in modifying and maintaining behavioural components may be particularly useful in reducing smoking in those individuals. For example, it has been found that behavioural components are significant in tobacco use by women. The present invention permits the development of behavioural learning on an individual/or group basis.

The compositions and treatment methods of the invention are also particularly suited to regulate nicotine metabolism in individuals or populations having high levels of CYP2A6. For example, Caucasians in North America have high levels of CYP2A6. An individual or population having a high level of CYP2A6 can be identified using our methods for measuring CYP2A6.

The compositions and methods of the invention also have the advantage of individualization and flexibility in treatment duration. The compositions and treatment methods are particularly suitable for severely dependent individuals, previous treatment failures, individuals unable to accept the current approach of complete cessation, treatment/prevention of relapse, or concurrent treatment with other methods such as the nicotine patch. It is expected that the compositions and treatments of the invention will decrease the doses of nicotine patch and all other forms of nicotine replacement therapies that are needed and will prolong the duration of action of the therapy and/or enforce their effectiveness in the treatment of tobacco dependence.

The methods and compositions of the invention in treating individuals with nicotine use disorders and nicotine-induced disorders are also useful in the treatment and prophylaxis of diseases or conditions, including nicotine-related disorders such as opioid related disorders; proliferative diseases; cognitive, neurological or mental disorders; and other drug dependencies in the individuals. Examples of such underlying diseases or conditions include malignant disease, psychosis, schizophrenia, Parkinson's disease, anxiety, depression, alcoholism, opiate dependence, memory deficits, ulcerative colitis, cholinergic deficits, and the like.

The methods and compositions of the invention may also be used in the prophylaxis and treatment of individuals having a condition which requires a reduction in CYP2A6 or CYP2B6. For example, CYP2A6 is known to metabolize several procarcinogens such as NNK (Crespi C L, et al., "A tobacco smoke-derived nitrosamine, 4-(methylnitrosamino)-1-(3-pyridyl)-1-butanone, is activated by multiple human cytochrome P450s including the polymorphic human cytochrome P4502D6," *Carcinogenesis*, 12(7):1197-201 (1991)), aflaxtoxin B1 (Yun C H, et al., "Purification and characterization of human liver microsomal cytochrome P-450 2A6," *Molec. Pharmacol.*, 40(5):679-85 (1991)); hexamethylphosphoramide (Ding X, et al., "Mossbauer studies on the metal-thiolate cluster formation in Fe(II)-metallothionein," *Eur. J Biochem.*, 171 (3):711-4 (1988)), and nitrosodimethylamine (Davies R L, et al., "Development of a human cell line by selection and drug-metabolizing gene transfection with increased capacity to activate promutagens," *Carcinogenesis*, 10:885-891 (1989); Fernandez-Salguero, et al. (1995)). Therefore, inhibitors of CYP2A6 may be useful in the prophylaxis (e.g., inhibition of CYP2A6 substrates thereby decreasing genotoxicity, cytotoxicity and/or mutagenicity) and treatment of malignant diseases, and, without limitation, the above-mentioned conditions and diseases.

Formulation and Dosing

The pharmaceutical compositions of the invention contain substances which inhibit CYP2A described in detail herein or substances identified using the methods of the invention. The active substances can be administered alone, but are generally administered with a pharmaceutical carrier etc. (see below), selected on the basis of the chosen route of administration and standard pharmaceutical practice.

The dosage administered will vary depending on the use and known factors such as the pharmacodynamic characteristics of the particular substance, and its mode and route of administration; age, health, and weight of the individual recipient; nature and extent of symptoms, kind of concurrent treatment, frequency of treatment, and the effect desired.

In some instances, instead of increasing the dosage of a compound, the kinetics of inhibition created by certain chemical compounds can be altered or enhanced by adding to the treatment protocol a second inhibitor to a substance (e.g., enzyme) that is capable of inhibiting the metabolism of the CYP2A6 inhibitor. By adding such a second inhibitor, the quantity of the CYP2A6 inhibitor will be maintained thus prolonging the beneficial effect of maintaining an elevated plasma concentration of nicotine. The use of such a second inhibitor is very beneficial since it facilitates treatment of individuals by maintaining substantially constant nicotine levels and acting locally on the kinetics of the CYP2A6 inhibitor. By using this approach, large dosages of centrally active compounds can be avoided.

Similarly, preexposure of an individual to an inhibitory substance sometimes can result in an inhibitory effect that will outlast the presence of the drug in the plasma or that will have a persistent effect in the individual despite the inhibitor's half life in the plasma. This phenomenon caused by preincubation or preexposure of an inhibitory substance can help increase the dose interval at which a dosage of the substance must be administered, decrease the chronic dose or enhance CYP2A6 inhibition. Furthermore, preexposure of an individual to one inhibitory substance can subsequently decrease the needed dose of a second inhibitor.

The appropriate dosage of a substance which selectively inhibits CYP2A6 is dependent upon the amount of CYP2A6 that is present in an individual's body. This amount is in turn dependent upon whether the individual contains two mutant alleles, one mutant allele or no mutant alleles at the CYP2A6 gene locus. In Example 1, we confirmed that such variations can exist in the genetic material of a population. It is, therefore, an aspect of this invention to provide a method for determining the CYP2A6 activity in an individual containing two mutant alleles, one mutant allele or no mutant alleles at a gene locus for the CYP2A6 gene, the method comprising the steps of:

(a) assaying a bodily sample containing deoxyribonucleic acid (i.e. a "DNA-containing bodily sample") from the individual to determine whether the individual contains two mutant alleles, one mutant allele or no mutant alleles at the CYP2A6 gene locus;

(b) determining the amount of CYP2A6 present in the individual; and (c) correlating the results of assaying in step (a) and the amount of CYP2A6 in step (b) to determine an appropriate dosage for that individual of a substance which (i) selectively inhibits CYP2A6 activity, or (ii) selectively inhibits transcription and/or translation of the gene encoding CYP2A6.

The individual recipient may be any type of mammal, but is preferably a human. Generally, the recipient is an individual having a CYP2A6 genotype associated with an active form of the enzyme. The CYP2A6 genotype of an individual and the existence of an active CYP2A6 enzyme in an individual may be determined using procedures described herein. For example, coumarin 7-hydroxylation has been used to measure CYP2A6 activity (Cholerton, et al. (1992); and Rautio, et al., (1992)). As discussed above, the methods and compositions of the invention may be preferably used in individuals or populations having high levels of CYP2A6, or in individuals where the behavioural components of smoking are significant.

For use in the treatment of conditions requiring regulation of nicotine metabolism to cotinine, by way of general guidance, a daily oral dosage of an active ingredient such as coumarin or methoxsalen can be about 0.01 to 80 mg/kg of body weight, preferably 0.01 to 20, more preferably 0.05 to 3 mg/kg of body weight. Ordinarily a dose of 0.03 to 50 mg/kg of coumarin, methoxsalen or tranylcypromine per day in divided doses one to multiple times a day, preferably up to four times per day, or in sustained release form is effective to obtain the desired results. In accordance with a particular regimen, coumarin or methoxsalen or tranylcypromine is administered once to four times daily for as long as necessary. While standard interval dose administration may be used the compositions of the invention may be administered intermittently prior to high risk smoking times, e.g., early in the day and before the end of a working day.

More than one substance described in detail herein or identified using the methods of the invention may be used to regulate metabolism of nicotine to cotinine. In such cases the substances can be administered by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chosen route of administration and standard pharmaceutical practice as described herein.

The substances for the present invention can be administered for oral, topical, rectal, parenteral, local, inhalant or intracerebral use. In an embodiment of the invention, the substances are administered in intranasal form via topical use of suitable intranasal vehicles, or via transdermal routes, using forms of transdermal skin patches known to those of ordinary skill in that art. To be administered in the form of a transdermal delivery system, the dosage administration will be continuous rather than intermittent throughout the dosage regimen. The substances can also be administered by way of controlled or slow release capsule system and other drug delivery technologies.

For example, for oral administration in the form of a tablet or capsule, the active substances can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and colouring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like.

Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain colouring and flavouring agents to increase patient acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl-paraben, and chlorobutanol.

The substances described in detail herein and identified using the methods of the invention can also be administered in the form of liposome delivery systems, such as small unilamellar vesicles, large unilamellar vesicles, and multi-lamellar vesicles. Liposomes can be formed from a variety of phospholipids, such as cholesterol, stearylamine, or phosphatidylcholines.

Substances described in detail herein and identified using the methods of the invention may also be coupled with soluble polymers which are targetable drug carriers. Examples of such polymers include polyvinylpyrrolidone, pyran copolymer, polyhydroxypropylmethacrylamidephenol, polyhydroxyethylaspartamidephenol, or poly-ethyl-eneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. The substances can also be affixed to rigid polymers and other structures such as fullerenes or Buckeyballs.

Pharmaceutical compositions suitable for administration contain about 1 milligram to 1500 milligrams of active substance per unit. In these pharmaceutical compositions, the active ingredient will ordinarily be present in an amount of about 0.5-95% by weight based on the total weight of the composition.

Suitable pharmaceutical carriers and methods of preparing pharmaceutical dosage forms are described in *Remington's Pharmaceutical Sciences*, Mack Publishing Company, a standard reference text in this field.

Co-administration with Oral Nicotine

In a particular embodiment, it has been found that specific inhibitors of CYP2A6, preferably methoxsalen and/or tranylcypromine, are particularly effective inhibitors of CYP2A6 and of the metabolism of an oral formulation of nicotine and as such, enhance the effect of oral nicotine replacement therapies. In other words, it has been found that these inhibitors are effective in inhibiting nicotine metabolism and thereby increasing plasma concentrations of nicotine, particularly when the nicotine is orally ingested thereby enhancing oral nicotine replacement therapies.

Thus, this invention provides a composition for enhancing the effect of oral nicotine replacement therapy, comprising an inhibitor of CYP2A6 and nicotine formulated for oral ingestion. In this method, the substances described in detail herein and/or identified using the screening method described above, together with nicotine, form the active ingredient, and are typically administered in admixture with suitable pharmaceutical diluents, excipients, or carriers suitably selected with respect to the intended form of administration, that is, oral tablets, capsules, elixirs, syrups and the like, consistent with conventional pharmaceutical practices.

Those of skill in the art will recognize that oral formulation within the invention can be in the form of: (i) a single composition comprising both the CYP2A6 inhibitor and nicotine, or (ii) a kit comprising independently administered compositions comprising the CYP2A6 inhibitor and nicotine, respectively. For independently administered compositions, the administration is preferably substantially contemporaneous. When the preferred CYP2A6 inhibitors methoxsalen and/or tranylcypromine are administered with oral formulations of nicotine the plasma concentrations of nicotine have increased over the plasma concentrations when nicotine is orally digested without administering the CYP2A6 inhibitor(s).

Combination of Inhibitors

The combination of an CYP2A6 inhibitor (e.g., coumarin, methoxsalen), and a CYP2B6 inhibitor (e.g., orphenadrine) enhances inhibition of nicotine metabolism to cotinine. Thus, a preferred embodiment of the invention provides a method for treating conditions requiring regulating nicotine metabolism to cotinine comprising administering an effective amount of a CYP2A6 inhibitor and an effective amount of a CYP2B6 inhibitor to selectively inhibit nicotine metabolism to cotinine. In a preferred embodiment of the invention, the CYP2A6 inhibitor is methoxsalen or an analog or derivative thereof, and the CYP2B6 inhibitor is orphenadrine, or an analog or derivative thereof. The inhibitors may be administered concurrently, separately or sequentially. Preferably, the administration of the inhibitors is substantially contempraneous. The doses of the CYP2A6 inhibitor and the CYP2B6 inhibitor are each selected so that each inhibitor alone would not show a full effect. The effective doses are those which are approximately the minimum doses adequate for enhanced inhibition of nicotine metabolism to cotinine. In one mode, the combination of inhibitors may be administered substantially contemporaneously with a source of nicotine, preferably nicotine formulated for oral administration. Pharmaceutical compositions containing combinations of CYP2A6 and CYP2B6 inhibitors may be prepared, and administered as described herein for the compositions containing CYP2A6 inhibitors. The pharmaceutical compositions preferably contain methoxsalen or an analog or derivative thereof, and orphenadrine, or an analog or derivative thereof, in concentrations of 1 to 1500 mg, and 25 to 400 mg, respectively.

Embodiments of the present invention will be illustrated with reference to the following examples which should not be construed as limiting the scope of the invention.

EXAMPLES

Example 1

Epidemiology Study

We examined the prevalence of CYP2A6 gene mutations in 126 tobacco dependent Caucasian smokers and 143 Caucasian individuals who had tried smoking, but who had never became tobacco dependent smokers (e.g., exposure controls). The objectives were two fold. The first was to determine the incidence of individuals who were deficient in CYP2A6 activity (e.g., homozygous for null CYP2A6 alleles). The second was to determine if slower CYP2A6 mediated nicotine metabolism, due to having null CYP2A6 alleles, decreased the chances of becoming a tobacco dependent smoker.

In this Example a study was conducted to assess the CYP2A6 genotype in a group of individuals and the effect of the CYP2A6 on the smoking behaviour of the individuals.

Subjects were unrelated healthy individuals each with 4 Caucasian grandparents and were divided into three groups. The first group comprised tobacco Dependent only (TD, DSM-IV ("DSM"=Diagnostic Statistician Manual of the American Psychiatric Association)) subjects including 76 males aged 19 to 52 years old (mean (SD): 31.1 years old (8.5 years)), and 57 females aged 20 to 70 years old (mean (SD): 31.4 years old (10.2)). The second group comprised Alcohol and Tobacco Dependent (AT, DSM-IV) subjects including 60 males aged 17 to 61 years old (mean (SD): 37.2 years old (9.94 years)), and 10 females aged 19 to 66 years old (mean (SD): 41.4 years old (11.89 years)). The third group was an exposure control group consisting of Never-Tobacco Dependent (NTD( subjects, who had previously tried smoking, but had never become dependent. This group included 86 males 19 to 59 years old (mean (SD): 29.2 years old (8.6 years)), and 77 females 19 to 58 years old (mean (SD): 27.4 years old (8.4 years)). All subjects completed a drug questionnaire and tobacco module (Heatherton, et al., "The Fagerstrom Test for nicotine Dependence: a revision of the Fagerstrom Tolerance Questionnaire," Br. J. Addict., 86(9):1119-1127 (1991)). All subjects had no other psychoactive drug dependencies, including alcohol (except of course for the AT group).

CYP2A6 genotyping of each subject was performed on genomic DNA isolated from peripheral leukocytes as described by Fernandez-Salguero, et al. (1995). Briefly, the assay consisted of a CYP2A6 gene-specific nested PCR amplification followed by a RFLP analysis.

Materials and Methods:

Primers Used for PCR Genotyping Assays:

TABLE 2

| Assay | Name | Sequence (5'-3') |
|---|---|---|
| CYP2A6*2 ($v_1$) and | F4 | CCTCCCTTGCTGGCTGTGTCCCAAGCTTAGGC (SEQ ID NO: 1) |
|  | R4 | CGCCCCTTCCTTTCCGCCATCCTGCCCCAG (SEQ ID NO: 2) |
| CYP2A6*3 ($v_2$) | E3F | GCGTGGTATTCAGCAACGGG (SEQ ID NO: 3) |
|  | E3R | TCGTGGGTGTTTTCCTTC (SEQ ID NO: 4) |

CYP2A6 Genotype

DNA is extracted from blood samples and quantified using routine extraction procedures. CYP2A6 genotype was determined using nested PCR and RFLP as described by Fernandez-Salguero, et al. (1995). The first amplification, which is CYP2A6 gene-specific, was used to increase the specificity for the CYP2A6 gene (versus other CYP2A genes). Exon 3 was utilized in the second amplification because both the CYP2A6*2 and CYP2A6*3 mutant alleles contain nucleotide changes leading to amino acid changes in this region of the CYP2A6 gene.

The first amplification was performed using the XL-PCR kit (Parkin-Elmer Co., Norwalk, Conn.). A 100 µl reaction mixture of 0.2 µM of primer F4 and R4, 200 µM dNTPs, 0.8 mM magnesium acetate, and 2 U of rTth1 DNA polymerase and 400 to 600 ng of genomic DNA used. The amplification was performed in a MJ DNA Engine (MJ Research, Inc., Watertown, Mass.) at 93° C. for 1 minute, 66° C. for 6 minutes and 30 seconds for 31 cycles.

The second amplification was performed in a reaction mixture containing 0.5 µM of primers E3F and E3R, 200 µM dNTPs, 1.5 mM $MgCl_2$, 2.5 U of Taq DNA polymerase (Gibco BRL, Life Technologies, Burlington, Ontario), and 2.5 µl of first amplification product, which was the template for the reaction. The reaction conditions were as follows: 94° C. for 3 minutes, followed by 31 cycles of 94° C. for 1 minute, 60° C. for 1 minute and 72° C. for 1 minute.

The second amplification yielded a PCR product 201 bp in length which was digested with Xcm I (New England Biolabs) and Dde I (New England Biolabs and Pharmacia Biotech) to detect the CYP2A6*2 and CYP2A6*3 mutations, respectively (cutting indicates the presence of the mutation). Concentrations of enzymes and PCR product, total volume and digestion time were determined empirically to optimize cutting efficiency with a minimal amount of time and enzyme. Xcm I digestion reactions were carried out at 37° C. for 2 hours in a 30 µl reaction mixture containing 1×NEBuffer 3 (100 mM NaCl, 50 mM Tris-HCl, 10 mM $MgCl_2$, 1 mM DTT pH 7.9 @ 25° C.), $dH_2O$, and 2 U of Xcm I. Dde I digestions were carried out at 37° C. for 2 hours in a 30 µl reaction mixture containing One-Phor-All (OPA) buffer (Pharmacia Biotech) and 2 U of Dde I. Digestion products were analysed on ethidium-stained 3% agarose gels.

Blood samples were obtained under consent from all subjects. Positive controls were donated by Drs. P. Fernandez-Salguero and H. Raunio. Negative controls used water in place of genomic DNA. Every genotyping reaction carried four randomly selected samples from a previous reaction to check for reproducibility.

Chi-Square tests were performed comparing distribution of CYP2A6 genotypes and alleles between groups (SAS). F-tests (check for unequal variance [SAS]), followed by a two-sample t-test (SAS) were used in comparing smoking patterns within smokers. Significance was at 5%.

It was postulated that individuals with impaired nicotine metabolism (i.e., carriers of at least one CYP2A6 defective or mutant allele) would experience greater aversive effects due to higher nicotine levels and not become smokers or would smoke at a decreased level when compared to individuals with active nicotine metabolism (i.e., individuals having CYP2A6*1/CYP2A6*1 genotype). Specifically, it was hypothesized that there would be an under-representation of individuals carrying defective CYP2A6 alleles in a tobacco dependent population.

Figure 5:
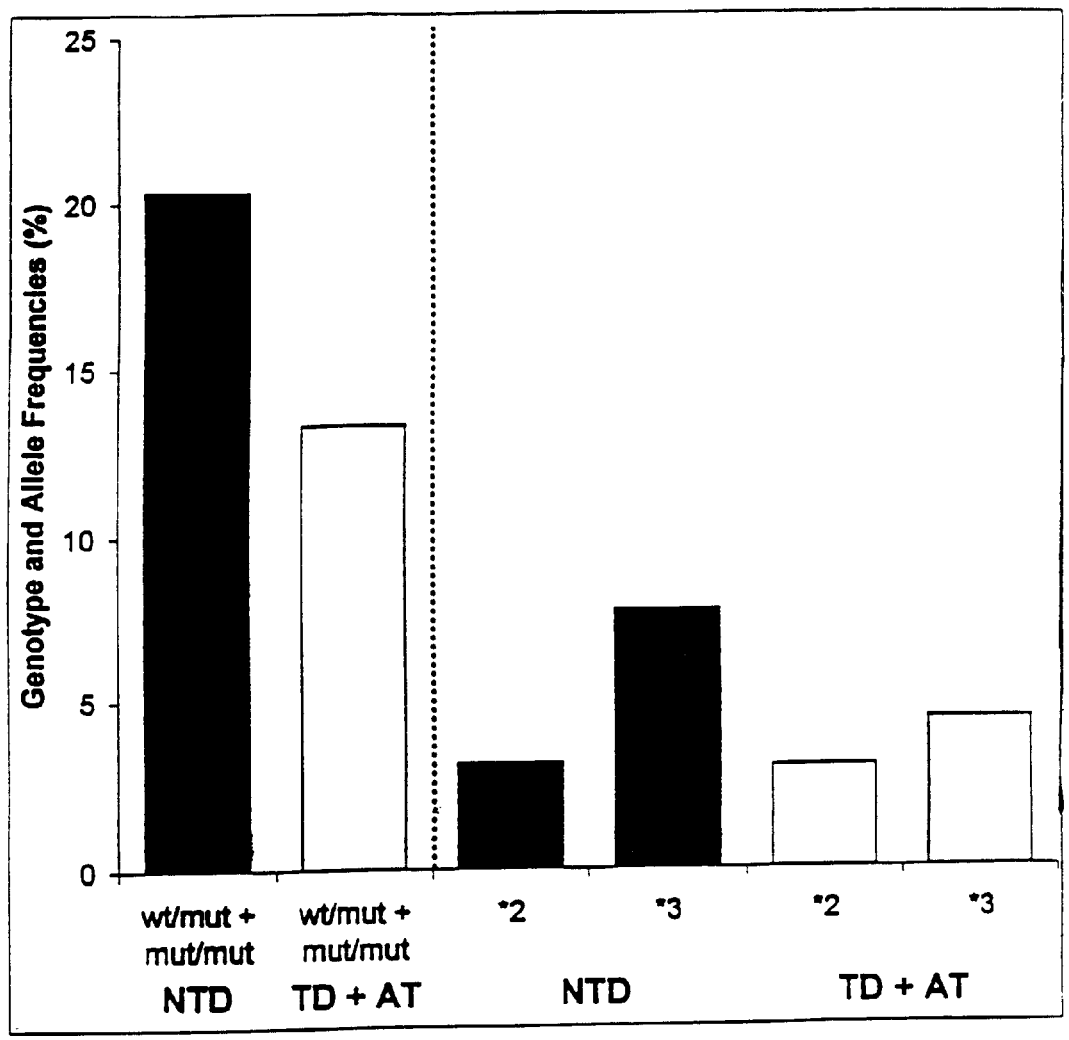
FIGS. 5 and 6 illustrate results of a study described in Example 1.

With reference to the results of the study, among the total dependent smokers (TD+AT), the frequency of individuals carrying 1 or 2 of the CYP2A6 defective alleles was lower than in the exposure control group (NTD): 13.3% vs. 20.2%, p=0.076, c-square; Odds Ratio of 1.66, C.I. 0.95-2.89—see FIG. 5. Further, both the CYP2A6*2 and CYP2A6*3 allele frequencies were lower in the dependent smokers (TD and AT) than in the exposure control group (NTD): CYP2A6*2: 3.0% versus 3.1% and CYP2A6*3: 4.4% versus 7.7%—see FIG. 5.

We further postulated that, within the group of those who smoke, those with deficient nicotine metabolism (i.e., carriers of at least one CYP2A6 defective or mutant allele) would smoke fewer cigarettes.

Figure 6:
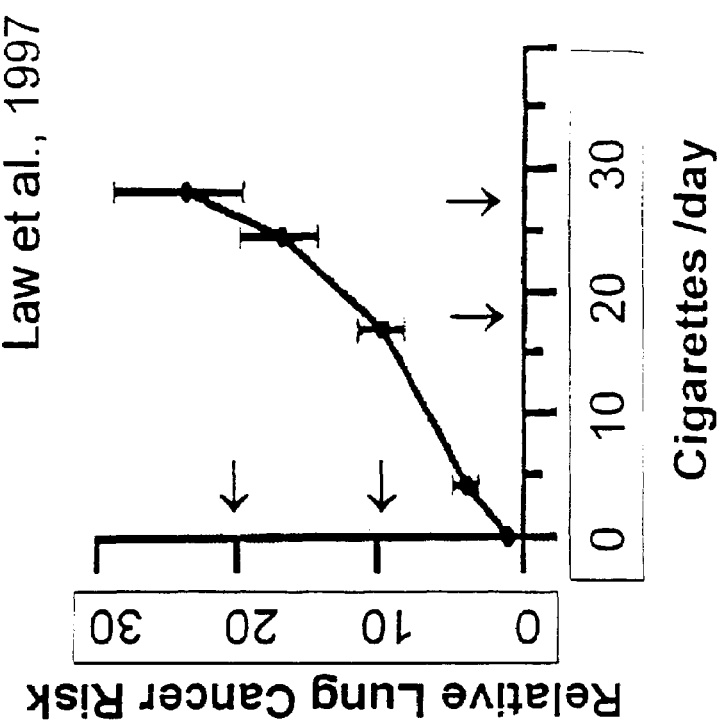
Figure 6:
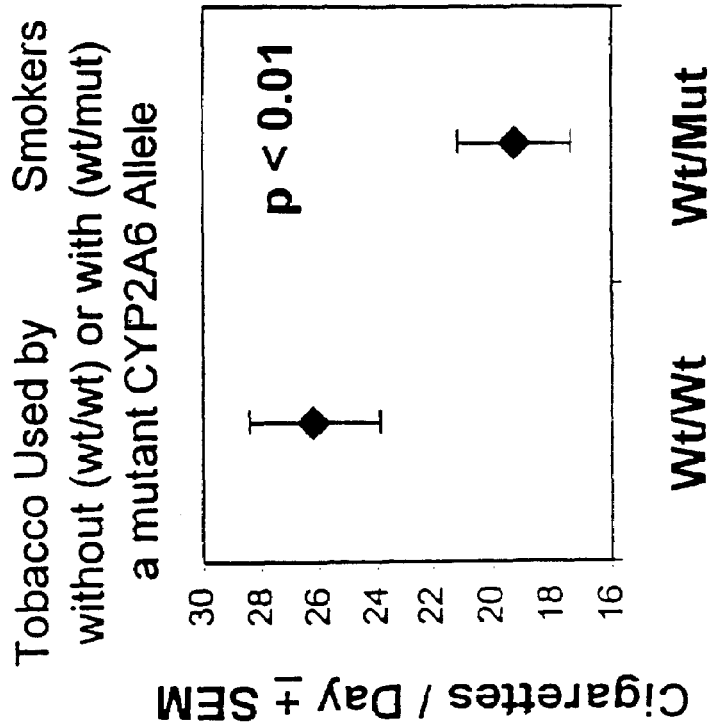

With further reference to the results of the study, within the TD group, those subjects which were homozygous for CYP2A6 active alleles smoked significantly more cigarettes per day and per week when compared with smokers who were heterozygous carrying a single CYP2A6 defective allele (i.e., one or both of CYP2A6*2 and CYP2A6*3): 23 versus 19 cigarettes per day, t test P=0.02, 125 versus 161 cigarettes per week, t test P=0.009—see FIG. 6.

As discussed above, nicotine is important in establishing and maintaining tobacco dependence; variability in nicotine pharmacokinetics could have a profound influence on whether individuals become smokers. The data produced in this study demonstrates an under-representation of individuals carrying 1 or 2 of the CYP2A6 defective alleles in a tobacco dependent population (TD+AT) when compared to a never tobacco dependent (NTD) control population. While not wishing to be bound by any particular theory or mode of action, this may be caused when individuals who carry CYP2A6 defective alleles, upon smoking, experience higher nicotine levels and greater aversive effects to the nicotine. As a result, the individual may discontinue smoking and be less likely to become tobacco dependent. Therefore, the data produced in this study indicates that individuals who carry 1 or 2 of the CYP2A6 defective or mutant alleles, and who try smoking, are at lesser risk for becoming tobacco dependent than individuals who have two active CYP2A6 alleles.

Further, as discussed above, it is well known that dependent smokers adjust their smoking behaviour in order to maintain blood and brain nicotine concentrations, and thus, variable nicotine metabolism could play a role in altering smoking patterns. The observation that dependent smokers who carry a single defective CYP2A6 allele smoke significantly fewer cigarettes when compared to homozygous wild-type smokers indicates that nicotine metabolism, as mediated by CYP2A6, is a significant determinant in the amount that dependent smokers smoke. In other words, heterozygosity in a single gene, namely the CYP2A6 gene, is affecting this complex drug taking behaviour.

The clinical implications of CYP2A6 genotype on tobacco dependence and smoking behaviour disclosed herein are widespread. Individuals who carry CYP2A6 defective alleles may have a decreased risk for cancer development because they have a decreased risk of becoming tobacco-dependent smokers. If they do become dependent smokers, the data produced in this study demonstrates that they would smoke less than those homozygous for active CYP2A6 alleles. There is clear evidence that the amount of tobacco smoked is related to increased risk for lung cancer (Law, et al. 1997))—see FIG. 6.

In addition, tobacco smoke contains a number of tobacco specific procarcinogen nitrosamines, such as N-nitrosodialkylamines—e.g., N-nitrosodiethylamine (the Merck Index, No. 6557), N-nitrosodimethylamine (The Merck Index, No. 6558) and 4-methylnitrosamino)-1-)3-pyridyl)-1-butanone (Crespi, et al. 1990; Yamazaki, et al. 1992). As these procarcinogens can be activated by CYP2A6, individuals who carry CYP2A6 defective alleles will be advantageously inefficient at bioactivating tobacco smoke procarcinogens to carcinogens.

Thus, in summary the data produced in the study of this Example demonstrates that a single genetically polymorphic gene, the CYP2A6 gene, is related, and in some cases predictive, of whether an individual becomes a smoker. In addition, if an individual becomes dependent on tobacco alone, the CYP2A6 gene variants alter the number of cigarettes that he/she smokes. Accordingly, the CYP2A6 genotype directly influences the risk for tobacco dependence, alters the amount of tobacco consumed, and plays a role in tobacco-related cancer susceptibility.

One envisaged application of the present invention is the genetic identification of an individual's risk for smoking and related cancers. Identification of high and low risk individuals will allow targeted prevention, treatment and education. Specifically this will involve the identification of an individual with a high and low risk for: (i) becoming a smoker (if the individual is a non-smoker), (ii) higher tobacco-consumption (if the individual is a smoker), and (iii) CYP2A6-related cancers.

Example 2

Coumarin Phenotyping Test and CYP2A6 Genotyping Test

A. Coumarin Test

Coumarin is a selective and specific substrate for human CYP2A6 and can be used to: (1) identify individuals who are potential therapeutic exclusions for use of CYP2A6 inhibitors; (2) for dosage refinement based on the initial level of activity of CYP2A6; and (3) for risk factor assessment in identifying individuals who will not benefit from the treatment or who may be at risk to toxicity from agents which are inhibitors and substrates themselves of CYP2A6. The Coumarin Test exists in two forms:

(1) Coumarin Test When Only Urine is Available

Figure 3:
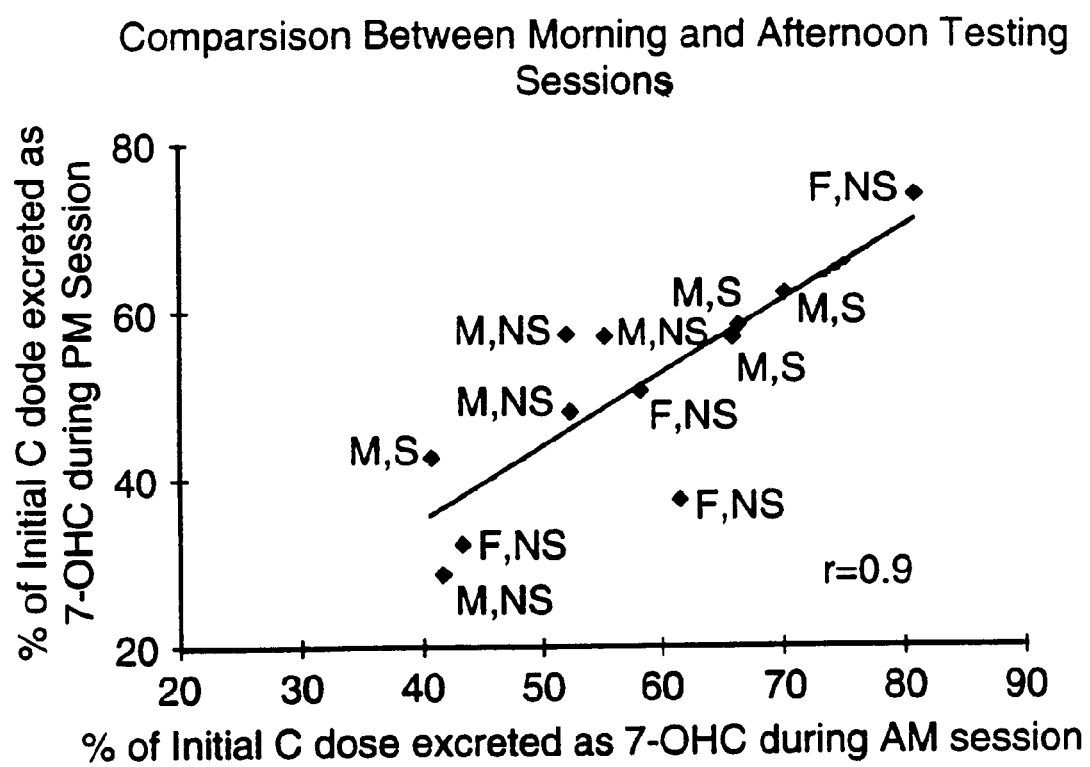
FIG. 3 is a graph illustrating a correlation between fasted morning and non-fasted afternoon coumarin (C) testing sessions.

Coumarin 5 mg formulated in a capsule or other dose form is administered orally to fasted individuals after voiding of residual bladder urine. Urine is collected for the first 2 hours and for the subsequent 6 hours. The amount of urinary excretion of the coumarin metabolite 7 hydroxycoumarin (free and conjugated) is determined by determining the concentration of these metabolites on the urine using an HPLC assay as described in an earlier example. The relative activity of CYP2A6 is reflected in the total amounts of 7 hydroxy-coumarin excreted in the sampling periods separately and combined and the activity can be expressed as the ratio of the percent coumarin excretion (amount excreted in the first 2 hours/amount excreted in 8 hours)× 100. This percent excretion ranges from values less then 20% in individuals without CYP2A6 activity to >80% in individuals with high activity. This test can be equally effectively and reliably be applied to smokers and non-smokers and may be used at any time of day with out apparent effect of the smoking condition or time of day on the results. The test demonstrates high within subject reproducibility with a linear r of >0.9. See FIG. 3 for results of a study in which smokers and nonsmokers were given coumarin in the morning and afternoon on each of 2 separate days. High within subject reproducibility and reliability is demonstrated.

(2) Coumarin Test When Plasma Samples Can Be Taken

In some clinical situations blood samples can be easily taken or are necessary as part of other clinical tests. In this situation, a plasma-based test of CYP2A6 activity has been developed and applied to individuals of known genotype. Individuals ingest coumarin 5.0 mg orally and 45 minutes later a blood sample is drawn in a heparinized (or other anticoagulant containing tube). The sample is spun and the plasma separated. The plasma is analysed by HPLC to quantitate 7 hydroxycoumarin (total after deconjugation with beta glucuronidase incubation). High analytical sensitivity is required in order to use 5.0 mg of coumarin. When such sensitivity is not available, the dose of coumarin may be increased up to 50 mg.

HPLC Analysis of 7-hydroxycoumarin in Urine and Plasma:

(1) Sample Preparation:

Urine or plasma samples (0.5 ml) are hydrolyzed with 0.2 ml of β-glucuronidase acetate buffer solution (15 mg/ml acetate buffer, 0.2 M, pH 5.0) at 37° C. for 30 min. Extraction is followed with 2 ml ether by vortex for 5 min and centrifuged at 3000 rpm for 10 min. Ether extract (1.2 ml) is transferred to another clean tube and dried down under nitrogen gas. The residue is reconstituted in the HPLC mobile phase (see below), and injected onto HPLC.

(2) HPLC Analysis:

The HPLC system consists of Hewlett Packard 1050 HPLC system (pump, autosampler and UV detector) and HP3396II integrator. The chromatographic separation was performed with an HP Spherisorb-ODS2 column (125×4 mm I.D., 5 μm). Samples were eluted with a mobile phase of acetonitrile:water:acetic acid of 150:850:2 (v/v/v) at a flow rate of 1.0 ml/min, and monitored by a UV detector at a wavelength of 324 nm for 7-hydroxycoumarin and 280 nm for coumarin. Samples are quantitatively determined by an external standard method.

The CYP2A6 activity is expressed as the concentration of 7 hydroxy-coumarin in the plasma at various points in time (e.g. 20, 30, 45 and 75 minutes) or as the ratio of coumarin/7 hydroxy-coumarin in the plasma at that time.

The preferred mode of use is a simple plasma sample at 20 or 30 minutes after the oral administration of coumarin in which both coumarin and 7-hydroxycoumarin are quantified and in which the coumarin to 7-hydroxycoumarin ration is used as the index of CYP2A6 activity.

Results:

Blank urine or plasma samples showed no interfering peak for 7-hydroxycoumarin or coumarin. Sensitivity of this method is 1 ng/ml urine or plasma. Intraday and inter-day variations are less than 10%. This analysis is linear from 1 ng to 4000 ng/ml.

Figure 4:
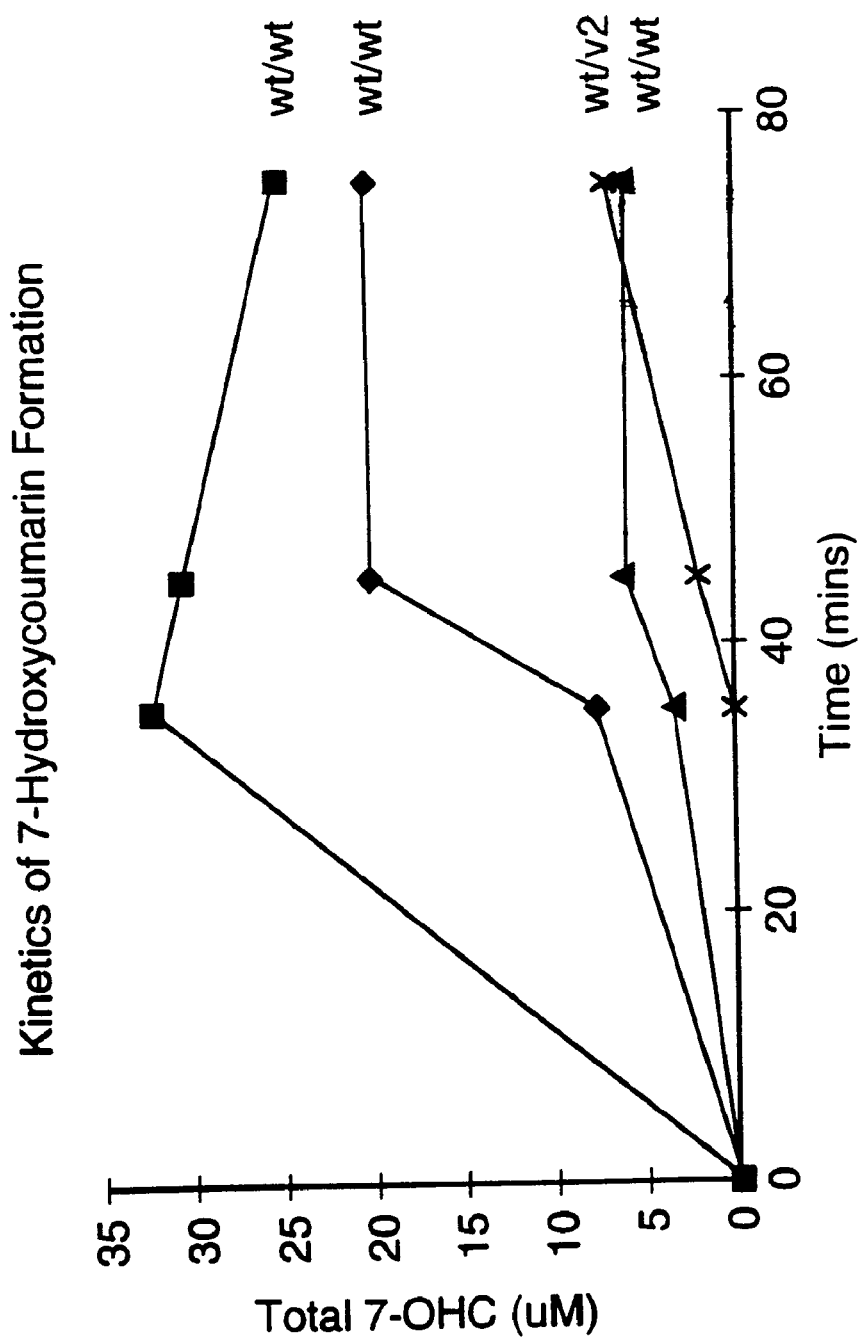
FIG. 4 is a graph showing a time course of total 7-hydroxycoumarin concentration detected in the plasma of subjects given 100 mg of coumarin.

FIG. 4 is a graph showing a time course of total 7-hydroxycoumarin concentration detected in the plasma of subjects given coumarin. FIG. 4 illustrates various time courses based on corresponding genotypes for CYP2A6.

B. CYP2A6 Genotyping Test

As for the CYP2A6 genotyping test, mutant alleles which decrease CYP2A6 activity in an individual can be screened in a DNA sample using the materials and screening method described in Example 1.

Example 3

In Vivo Phenotype Assay

The plasma kinetics of nicotine and coumarin were compared after oral administration in 10 smokers and 9 non-smokers (12 males, 7 females) of known CYP2A6 genotype. The dose of nicotine was 4.0 mg (expressed as base) and the dose of coumarin was 50 mg. The plasma concentration of nicotine, cotinine, coumarin and 7-OH-coumarin were measured as described above.

Optimal separation of *1/*1 (wild type homozygotes, n=13) and heterozygotes (*1/*2; *1/*3, n=4) and homozygotes (*2/*2, n=2) was found at 45 min with coumarin by measuring its metabolite 7-OH-coumarin (7-OH-coumarin [μM] *1/*1=5.6±2.9; *1/*2 or *1/*3–3.8±1.1, p=0.04).

Optimal separation was found at 90 min with nicotine (nicotine [nM] *1/*1=24±15; *1/*2 or *1/*3=29±12; *2/*2=52±3; *2/*2 vs. *1/*2 or *1/*3, p=0.01; *2/*2 vs. *1/*1, p=0.0001). The use of the coumarin/7-OH-coumarin or nicotine/cotinine ratio did not improve separation.

Cotinine (nicotine metabolite) was significantly more slowly produced in *1/*2 or *1/*3 initially, but late in sampling cotinine was actually higher in *1/*2 or *1/*3, suggesting a role for CYP2A6 in cotinine metabolism. The slope of the curve for appearance vs. time was significantly less for 7-OH-coumarin and greater for nicotine in *1/*2 or *1/*3 compared to *1/*1, as were the areas under the curves, indicating differences in bioavailability, rates of absorption and metabolism. The area of the curves for 7-OH-coumarin and for nicotine were inversely correlated (p=0.08 (Spearman rank), n=18). One *1/*1 individual with 4-fold greater 7-OH-coumarin production and one *2/*2 individual with high coumarin and low nicotine metabolism were identified, suggesting that CYP2A6 gene variants not detected with current PCR procedures exist.

These data indicate CYP2A6 genotype is an important determinant of time course for nicotine disposition in vivo. These data also indicate that an in vivo assay of CYP2A6 reflects the phenotype of the individual, and that the phenotypic determination provides information on the genotype of that individual.

Example 4

Tissue Localization of CYP2A6 Expression

It was determined if the CYP2A6 enzyme was expressed in tissues in which tobacco-related cancers occur (e.g., lung and bladder). In order to determine whether CYP2A6 was expressed in tissues which were subject to tobacco-related cancers, the tissue distribution of the CYP2A6 mRNA was examined in various human tissues using Northern blot analysis. Briefly mRNA from numerous tissues was loaded onto gels and separated by electrophoresis. The mRNA was then transferred to membranes and probed with radioactive CYP2A6 cDNA probe. Evidence was found for the expression of CYP2A6 in uterus, ovaries, colon, small intestine, testis, bladder, heart, stomach, prostate, skeletal muscle, pancreas and lung. These data suggest that in addition to the possibility that CYP2A6-activated carcinogens from the liver might cause cancer in various tissues there could also be in situ activation of the procarcinogens in a number of human tissues.

Example 5

Epidemologic Study for Cancer Risk

In addition to the role that null CYP2A6 alleles have in reducing the rate of nicotine-dependence and the amount smoked if one becomes dependent, procarcinogens found in tobacco-smoke can be activated by CYP2A6. In order to determine whether there was a significant contribution to cancer rates due to activation of procarcinogens by CYP2A6, independent of its role in smoking, a study was made of individuals with a tobacco-related cancer who were non-smokers. These individuals were passively exposed to tobacco smoke procarcinogens, therefore providing a group in which the role of the CYP2A6 null alleles in the activation of procarcinogens could be tested independently of the role of this enzyme on smoking behaviour. It was found that 14.3% of non-smokers who had bladder cancer (a tobacco-related cancer) carried a null allele for CYP2A6. In contrast, in the control population who were non-smokers and did not have bladder cancer, the frequency of null allele carriers was 24.1%.

This demonstrates that individuals who carry null alleles for CYP2A6 are less likely to get a tobacco-related cancer due to their decreased activation of procarcinogens to cancer-causing carcinogens.

Example 6

Effect of Methoxsalen, a CYP2A6 Inhibitor, on Activation of NNK, a Procarcinogen, to its Metabolites NNAL and NNAL Glucuronide The effect of methoxsalen, CYP2A6 inhibitor, on nicotine metabolism and NNAL production was studied in eleven (n=6 females, 5 males) tobacco dependent smokers. Subjects were recruited only if they smoked at least 15 cigarette per day, and were required to smoke the same number of cigarettes each day, on all four study days. During assessment, blood was taken to be analyzed for plasma nicotine and cotinine levels, as well as for CYP2A6 genotyping. Breath carbon monoxide was also measured.

The four test days were broken down into one placebo day (no drug given) (day 1) and three methoxsalen (10 mg t.i.d. p.o.) treatment days 2, 3, 4), such that medication was taken at 8:00 a.m., 3:00 p.m. and 10:00 p.m. each day. During each study day a smoking log was completed. This log asked subjects to document the number of cigarette smoked from 8:00 a.m. to 3:00 p.m. to 10:00 p.m., and 10:00 p.m. to 8:00 a.m. Study days 1 and 2 could be separated, but days 2, 3 and 4 were required to be consecutive.

On both study days 1 (placebo) and 4 (treatment), a 24 h urine collection was initiated on waking. At 2:00 p.m. blood was drawn for nicotine and cotinine analysis and breath carbon monoxide was measured. On day 4, a second blood sample was taken for methoxsalen analysis. Urine samples can be analyzed for 24 h NNAL, NNAL glucuronide, creatinine and cotinine.

Methoxsalen increased plasma nicotine by 17% (23.0 to 27 ng/ml); decreased breath CO by 11% (22.5 to 20.5 ppm) and increased the ratio of plasma nicotine to breath CO (an index of tobacco smoke exposure) by 30% (1.1 to 1.43, p=0.033). The larger decrease in the index of smoke exposure indicates: 1) the smokers decreased the intensity of their smoking due to inhibition of CYP2A6 and slowed nicotine elimination despite being told to not change their smoking; 2) methoxsalen in these doses is an effective inhibitor of CYP2A6; and 3) methoxsalen and other CYP2A6 inhibitors will decrease production of NNAL or related substances and the activation of other carcinogens in vivo.

Example 7

Influence of the CYP2A6 Null Alleles on Tobacco-smoke Exposure Leading to Lung Cancer The effect of the CYP2A6 null alleles on activation of procarcinogens was examined in an epidemiological study of lung cancer. The allele frequencies in DNA samples from 227 individuals with lung cancer was determined. Following diagnosis of lung cancer and resection of the tumor and surrounding lung tissue, the DNA was extracted and genotyped for CYP2A6. The population was principally smokers or ex-smokers. Among those from whom detailed smoking histories were available, we were able to assess the number of pack-years of smoking (20 cigarettes/day for one year=one pack-year) as a measure of procarcinogen exposure, prior to detection of the lung cancer. Those individuals who had wt/wt CYP2A6 activity required an average of only 45 pack-years prior to lung cancer detection. In contrast, those individuals with a CYP2A6 null allele, who activate less of the procarcinogens, required considerably more procarcinogen exposure prior to detection of lung cancer (e.g., 54 pack-years). Thus those individuals with decreased CYP2A6 activity activate less of the tobacco-smoke procarcinogens and require greater exposure before lung cancer is detected.

It was also observed that the number of individuals with the CYP2A6V1 allele in the lung cancer population was decreased relative to a non-lung cancer control population, consistent with the relative protection against cancer offered by decreased procarcinogen activation. This was observed in both non-smokers and smokers with lung cancer relative to their respective controls.

In addition, all of the individuals who had ras oncogene mutations in the tumor tissues were full activity CYP2A6 wildtype indicating a decreased risk for oncogene mutations in those individuals with decreased CYP2A6 activity (e.g., carriers of the CYP2A6 null alleles). Ras oncogene mutations are predictive of a poorer treatment outcome and faster growing tumors relative to those tumors without ras oncogene mutations. This suggests that individuals with CYP2A6 null alleles, were less likely to have mutated ras oncogenes, and were more likely to have a better treatment prognosis.

These data indicate the utility in assessing CYP2A6 alleles for estimation of cancer risk (null alleles being associated with decreased risk for lung cancer) and that inhibition of CYP2A6 will decrease procarcinogen activation decreasing the risk for cancer.

Example 8

Effect of CYP2A6 Inhibition on the Bioavailability of Oral Nicotine

An in vivo study was undertaken to determine the effect of CYP2A6 inhibition on the bioavailability of oral nicotine. In particular, the study compared the kinetic effects of nicotine cotreatment with methoxsalen 30 mg, tranylcypromine 10 mg and of placebo (i.e., nicotine only) p.o. on the bioavailability of nicotine 4 mg p.o (expressed as base; nicotine bitartrate salt was actually administered), and the acute safety and acceptability of the three cotreatments. Additionally, preliminary information was obtained about effects on nicotine craving following these cotreatments.

The subjects for the study were smokers following a specified abstinence regimen as set out below. There were 12 subjects.

The smokers underwent placebo p.o. and two separate cotreatments 30 (methoxsalen 30 mg and tranylcypromine 10 mg) accompanying nicotine 4 mg p.o. During a 4-hour test session, blood and urine samples were collected for kinetic measures, and physiologic and subjective measures were collected. The treatment order was randomized and counterbalanced and the drug presentations were single-blind, namely, the subjects were unaware of what drug they were taking.

All of the subjects had the following characteristics:
(a) age at least 21;
(b) current consumption of at least 25 cigarettes per day;
(c) DSM IV current tobacco dependence;
(d) nicotine dependence as indicated by a score of at least 3 on the Fagerström Test of Nicotine Dependence (FTND);

(e) no regular use of tobacco in any form other than cigarettes;
(f) ability to abstain from cigarette smoking and from caffeine for up to 12 hours;
(g) agreement and ability to maintain the use of any therapeutic drugs on a consistent schedule across the study days.

All of the subjects did not have any of the following characteristics:
(a) known sensitivity to methoxsalen or chemically similar compounds;
(b) known excessive photosensitivity;
(c) current use of any antidepressants, sympathomimetics, CNS depressants, hypotensive agents, or antiparkinsonian drugs (because of possible adverse tranylcypromine interactions);
(d) body weight <51 kg (30 mg methoxsalen is not recommended for use below this body weight);
(e) pregnancy or lactation;
(f) risk of pregnancy (females who are sexually active with male partners and not using highly effective contraceptive precautions, defined as surgical sterilization of either partner, oral contraceptives, barrier and spermicide, or condom and spermicide);
(g) liver damage, blood dyscrisias (counterindications for tranylcypromine);
(h) symptoms suggestive of cardiac disease or hypertension;
(i) any other medical or psychiatric condition that requires further investigation or treatment or that is a contraindication for any of the proposed study drugs;
(j) current desire or attempts to quit smoking within the expected duration of the study series; and
(k) any other condition likely to interfere with compliance with the study schedule or successful collection of study measures.

There were two separate study schedules for subjects tested in the morning and in the afternoon. On both schedules, each subject abstained from tobacco, food, beverages (i.e., other than water), and any inconsistently used drugs from midnight before each study day but continued to take any regularly scheduled drugs allowed by the protocol (e.g., oral contraceptives, daily vitamins).

Subjects on the morning schedule continued such abstinence until arrival at the test site at approximately 8 am. Subjects on the afternoon schedule ate a normal-sized breakfast, including at most one cup of a caffeinated beverage and one cigarette before 9 am. From 9 am then to approximately 1 pm subjects in the afternoon session resumed the abstinence regimen until arrival at the test site.

Before baseline measures were taken, a breath CO sample (Ecolyzer) was taken to assess compliance with the smoking abstinence (<10 ppm expected). The subsequent daily schedule is set out in Table 3. All measurements were with respect to a time zero at 9:00 am or 2:00 pm, at which time a nicotine capsule and a cotreatment are taken p.o. Each SMS cycle consisted of heart rate, blood pressure, and subjective measures. A standard breakfast or lunch (but without caffeine) was served after the blood sample at +1:00 h.

TABLE 3

| Time Elapsed | Event |
| --- | --- |
| −00:45 | Prepare the subject |
| −00:30 | Blood sample (8 mL) taken - #1 |
| −00:15 | SMS cycle #1 |

TABLE 3-continued

| Time Elapsed | Event |
| --- | --- |
| 00:00 | All capsules p.o. |
| 00:30 | Blood sample (8 mL) taken - #2 |
| 00:50 | SMS cycle #2 |
| 01:00 | Blood sample (8 mL) taken - #3 |
| 01:30 | Blood sample (8 mL) taken - #4 |
| 01:50 | SMS cycle #3 |
| 02:00 | Blood sample (8 mL) taken - #5 |
| 2:50 | SMS cycle #4 |
| 03:00 | Blood sample (8 mL) taken - #6 |

Subjects were medically assessed for discharge no earlier than +2:00 and were discharged after all measures were completed at +3:00 h.

Subjects were not allowed to smoke until after their discharge. The schedule was in certain circumstances delayed by up to 20 minutes, consistent across the four days, in order to allow three subjects to be tested on the same day.

Each subject was tested on two non-consecutive days in a week for three separate weeks and maintained a morning or afternoon schedule consistently.

Sterile nicotine bitartrates was obtained by the Pharma Centre from Sigma Chemical. The reported purity was >99.5% which was confirmed by HPLC. The nicotine bitartrate powder was measured on a precision balance accurate to within 1 μg, measured into portions containing 4 mg of the nicotine base, and then encapsulated. Capsules were filled to a tolerance of +2% of their nominal mass of nicotine powder.

Methoxsalen is marketed in Canada in two forms, one of relatively low bioavailability (trade name Oxsoralen®) and two of approximately twice as high a bioavailability (Oxsoralen-Ultra® and Ultra MOP®). The package insert for Ultra MOP® (Canderm Pharmacal Ltd.) recommends a daily dose of 30 mg to 50 mg for any patient weighing 51 kg or more. Subjects were restricted to a minimum body weight of 51 kg, in order to allow the use of a fixed 30 mg dose for all subjects; the dose was not adjusted for larger subjects.

Capsules of methoxsalen 10 mg and tablets of tranylcypromine 10 mg (Parnate®) were used in their marketed forms. Because it was a randomized but singleblind study, subjects were able to recognize that the capsule forms and number varied from day to day, but they did not know which form represented which drug.

Lactose tablets were used for the placebo.

For the first four days, each day's drug supply consisted of one or three capsules, as set out in Table 4, in addition to nicotine 4 mg. The investigators were unaware of the distribution to preserve random allocation.

The nicotine and other capsules were taken simultaneously.

A separate, printed, reference copy of each subject's treatment randomization code was provided to the investigators after the drugs were dispensed.

TABLE 4

| Active Drug, Capsule Form | Administered Dosage |
| --- | --- |
| placebo | 1 × coumarin-size placebo |
| methoxsalen, 30 mg | 3 × methoxsalen, 10 mg |
| tranylcypromine, 10 mg | 1 × tranylcypromine, 10 mg |

Using an indwelling venous catheter, 8 mL blood samples were collected at the elapsed times set out in Table 3. These samples were analyzed for nicotine, cotinine and inhibitor concentration.

Two separate urine samples were collected, a baseline just prior to the capsules and a three-hour pooled sample. Each urine sample was analyzed for nicotine and cotinine content.

Plasma and urinary nicotine and cotinine (and also the conjugates in urine) were determined using an HPLC method with a UV detector. Specifically, 1 mL of sample, 50 µL (2 µg/mL) of the internal standard (N-ethylnornicotine) and 1 mL of trichloroacetic acid (10%) were pipetted into each tube (12 mL). The tube was capped, vortex-mixed for a few seconds, and then centrifuged at 30,000 g for 5 minutes. The clear supernatant was decanted in a second tube. To this protein-free plasma extract was added 0.5 mL of a 5 M potassium hydroxide solution and 6 mL of methylene chloride. The second tube was then capped, agitated for 30 minutes in a horizontal shaker and then centrifuged to separate the phases. The aqueous phase (the top layer) was aspirated, and 3.0 mL of 0.5 N hydrochloric acid solution was added to the organic phase and vortex-mixed for 30 seconds. The phases were separated by centrifugation, and the aqueous phase was transferred to a clean tube with 0.5 mL of 5 M potassium hydroxide solution, followed by addition of 5 mL of methylene chloride and vortex mixing for 30 seconds. The phases were separated by centrifugation, the aqueous (top) layer was aspirated, and 200 ml methanolic hydrochloric acid (10 mmol HCl in methanol) was added to the remaining solution and mixed gently. The organic solvent was then evaporated under nitrogen in a water bath at 40° C. The sides of the tube were washed with 200 µL of methanolic hydrochloric acid and the solution was evaporated. The residue was reconstituted in 100 µL of 30% methanol and 90 µL thereof was injected in the HPLC column.

The chromatographic separation was performed with a Supelco™ 5-8347 LC-8-DB (150×4.6 mm, 5 µm). The sample was eluted with a mobile phase of 0.34 M citric acid buffer:acetonitrile, 800:45 (v/v) containing 0.34 M $KH_2PO_4$, 1-heptane sulphonate (671 mg) and triethylamine (5 mL) with a flow rate of 1.3 mL/min, and monitored by a UV detector at I=260 nm.

The sensitivity of the nicotine assay is <1 ng/mL and that of the cotinine is <5 ng/mL. Conjugates in urine were determined after hydrolysis with β-glucuronidase, when appropriate.

Figure 7:
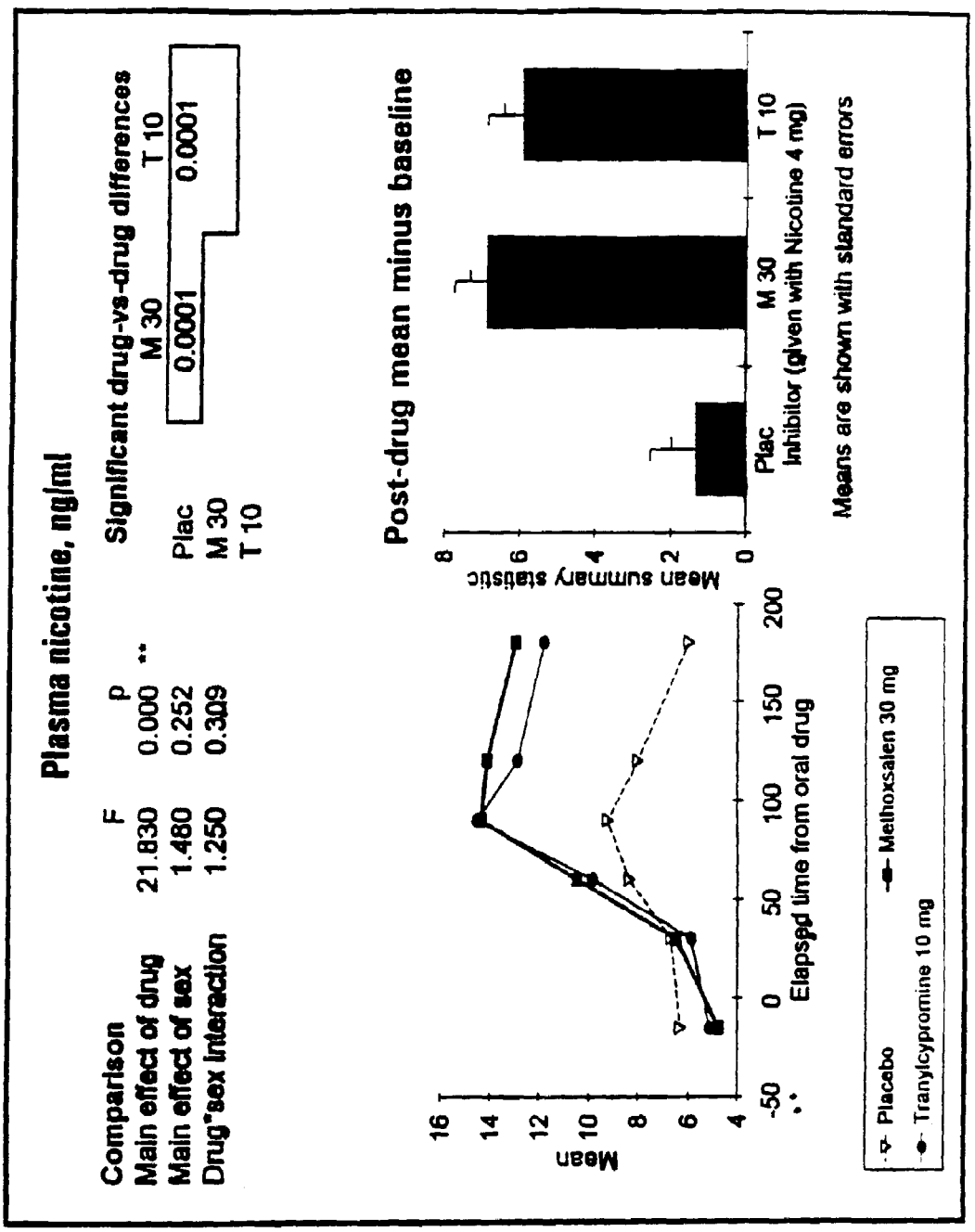
FIG. 7 illustrates mean plasma nicotine concentrations in the study reported in Example 8.

Plasma nicotine concentration was determined using the above-mentioned assay, and the results are illustrated in FIG. 7 as the mean for all subjects.

Cardiovascular measures, transduced by a Hewlett/Packard 78352C Adult Patient Monitor and recorded directly into a computer included heart rate and blood pressure (while seated).

Using a visual analog scale, each subject was asked to evaluate, on a scale of 0 to 100, his/her current desire to smoke a various points in time, both pre- and post drug administration (Appendix A).

For the purposes of establishing clinical kinetic differences and describing kinetic parameters, the primary dependent variable was the 3-hour trapezoidal-rule nicotine AUC.

FIG. 7 illustrates the mean plasma nicotine concentrations measured just prior to oral drug administration and for three hours thereafter (during which no smoking was allowed). As illustrated, the combined methoxsalen/nicotine and tranylcypromine/nicotine treatments both induce an increase in mean plasma nicotine concentration that is at least four times as large as that induced by the placebo/nicotine combination.

Figure 8:
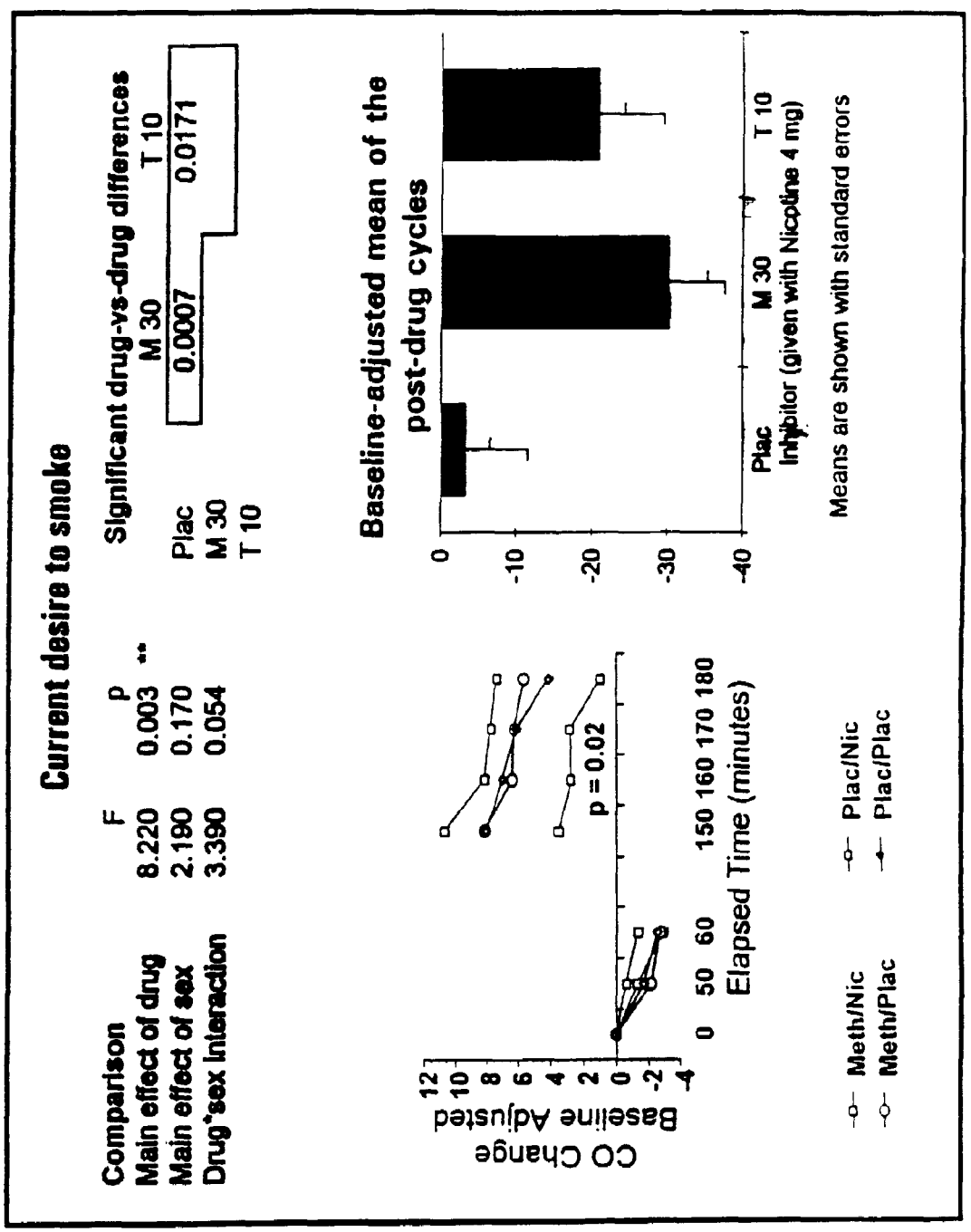
FIG. 8 illustrates current desire to smoke in the study reported in Example 8.

FIG. 8 illustrates the self-rated "Current desire to smoke" evaluation, using a visual analog scale scored from 0 to 100. As illustrated, both the methoxsalen/nicotine and tranylcypromine/nicotine combination reduced the desire to smoke significantly more than does the placebo/nicotine combination.

Example 9

Effects of Metabolically Enhanced Oral Nicotine Replacement Therapy on Short-term Smoking Behaviour A study was undertaken to determine the effects of metabolically enhanced oral nicotine replacement therapy on short-term smoking behaviour.

Because nicotine is the addictive agent in tobacco dependence, and smokers regulate their brain nicotine within a fairly narrow individual concentration band, any effective non-smoking method of nicotine delivery should result in a decrease in smoking by allowing smokers to maintain plasma nicotine without resorting to smoking and, in some cases, reduce the secondary reinforcement of smoking behaviour as a component of eventual smoking cessation. This effectiveness can only be enhanced if the mechanism for ensuring effective delivery also delays the clearance of plasma nicotine after the absorption stage. A model for testing the acute behavioural effects of this treatment strategy is provided in a previous study of the effectiveness of nicotine gum (Nemeth-Coslett R, et al., "Nicotine gum: dose-related effects on cigarette smoking and subjective ratings," *Psychopharmacology,* 92(4):424-30 (1987)), where smoking in a 90-minute test period was significantly affected by the nicotine content of the gum.

In this Example, all four combinations of placebo/methoxsalen and placebo/nicotine were tested (i.e., (i) placebo methoxsalen and nicotine; (ii) methoxsalen and nicotine, (iii) methoxsalen and placebo nicotine; and (iv) placebo methoxsalen and placebo nicotine).

This Example demonstrates: the kinetic effectiveness of methoxsalen-enhanced oral nicotine replacement therapy in briefly abstinent smokers; and the behavioural effectiveness of methoxsalen-enhanced oral nicotine replacement therapy in briefly abstinent smokers.

There were 11 subjects. The subject inclusion and exclusion criteria used in Example 8 were used in this Example.

The subjects each underwent four separate sessions of 90 minutes smoking abstinence followed by 90 minutes ad lib smoking, where the following four treatments were each presented double-blind once during the first four study days, in randomized, counterbalanced order, during the abstinence period: (i) placebo methoxsalen with placebo nicotine, (ii) placebo methoxsalen with 4 mg nicotine, (iii) methoxsalen 30 mg with placebo nicotine, and (iv) methoxsalen 30 mg with 4 mg nicotine. Methoxsalen 10 mg capsules were used, as in Example 1, and capsules of royal jelly were used as the placebo. Capsules were dispensed in an opaque vial, and neither subjects nor investigators viewed the capsules prior to the subjects placing them directly into their mouths.

Nicotine 4 mg capsules were prepared as in Example 8, and corresponding royal jelly capsule placebos containing only lactose were also prepared. Subjects took the three methoxsalen/placebo capsules and one nicotine/placebo capsule either all at once or consecutively.

The treatment order was counterbalanced across the two sexes and the two times of day to the extent possible. The order of the treatments was determined by a computerized randomization program. The treatment was double-blind.

As in Example 8, there was a morning and afternoon schedule.

Study sessions were scheduled twice each day, with three subjects running simultaneously, beginning at 8:30/8:40/8:50 am and at 1:00/1:10/1:20 pm. Sessions lasted for about 4 hours. Prior to each session, subjects were allowed to smoke, eat, and drink caffeine as they desired up to 90 minutes before each session, at which time they stopped eating and drinking (other than water). Each session began 60 minutes before a drug/placebo/nicotine were taken. The precise schedule is set out in Table 5.

TABLE 5

| Time Elapsed | Event |
|---|---|
| −00:40 | Pre-abstinence cigarette |
| −00:30 | Abstinence begins |
| −00:10 | 1. Blood sample (8 mL) taken - #1 |
|  | 2. CO measured |
|  | 3. Questions 1-9 in Appendix C |
| 00:00 | 1. CO measured |
|  | 2. All capsules p.o. |
| 00:50 | 1. Blood sample (8 mL) taken - #2 |
|  | 2. CO measured |
|  | 3. Questions 1-12 in Appendix C |
| 00:59 | 1. CO measured |
|  | 2. Video camera on |
| 01:00 | 1. Abstinence ends |
|  | 2. Free smoking begins |
| 02:30 | 1. Video camera off |
|  | 2. Free smoking ends |
|  | 3. Blood sample (8 mL) taken - #3 |
|  | 4. CO measured |
|  | 5. Questions 1-17 in Appendix C |
|  | 6. Abstinence resumes |
| 02:40 | CO measured |
| 02:50 | CO measured |
| 03:00 | CO measured |

The first post-cigarette abstinence period lasted 90 minutes, of which the last 60 minutes were post administration of placebo/drug/nicotine. The second abstinence period was included to facilitate repeated measures of the post-smoking breath carbon monoxide (CO). On the three occasions when blood samples were collected, the subject also answered a brief questionnaire about possible study drug symptoms and effects and about desire to smoke. Additionally, on the third occasion, there were also questions about perception of the cigarettes smoked during the free smoking period. This questionnaire (see Appendix A) is based on the one used in the nicotine gum study (Nemeth-Coslett, et al. (1987)).

During the free smoking period, subjects were allowed to smoke as they wished, providing only that they stay within the area of the room visible to the video camera, and to eat light snacks and drink non-caffeinated beverages.

The primary dependent variable measured was the change in breath CO during the free-smoking period, measured as the mean of the three samples 10, 20, and 30 minutes post-smoking minus the mean of the two samples 10 and 0 minutes pre-smoking. Other dependent variables measured were the change in plasma nicotine between 0 and 150 minutes post-drug, the responses to the symptom and rating scales, the consumption of tobacco in the free smoking period (measured as the weight of butts remaining subtracted from the weight of the same number of unsmoked cigarettes), and the puff timing and count from analysis of the videotapes.

Dependent variables were evaluated in an analysis of variance, with the treatment drug combinations as the primary independent variable of interest, with sex, morning/afternoon schedule, and treatment order as additional explanatory variables removed from the error term.

The results of the study of Example 10 will now be discussed with reference to FIGS. 9-14.

Figure 9:
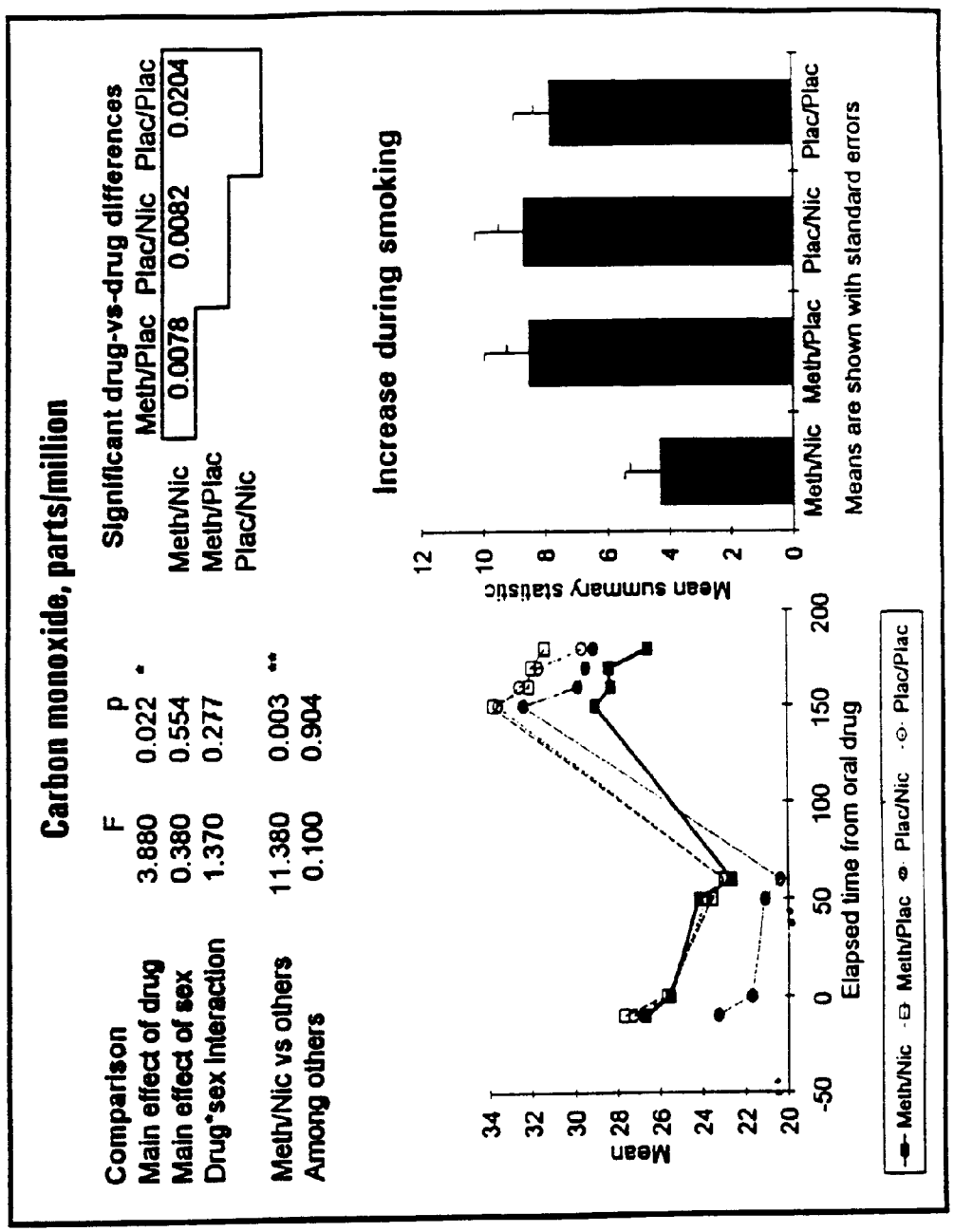
FIG. 9 illustrates mean breath carbon monoxide in the study reported in Example 9.

FIG. 9 illustrates the mean breath carbon monoxide concentration measured just prior to oral drug administration, 60 minutes later (no smoking allowed) and after the 90 minute free smoking period. As illustrated, the combined methoxsalen/nicotine treatment results in a significant and large reduction in the increased in breath carbon monoxide during the smoking phase. The carbon monoxide levels increased in the combined methoxsalen/nicotine treatment group only 30% of that seen in the other conditions, reflecting a large reduction in smoking and smoke exposure. This reduction may be attributable due to any combination of fewer puffs, shallower puffs and/or puffs held for a shorter duration before exhalation.

Figure 10:
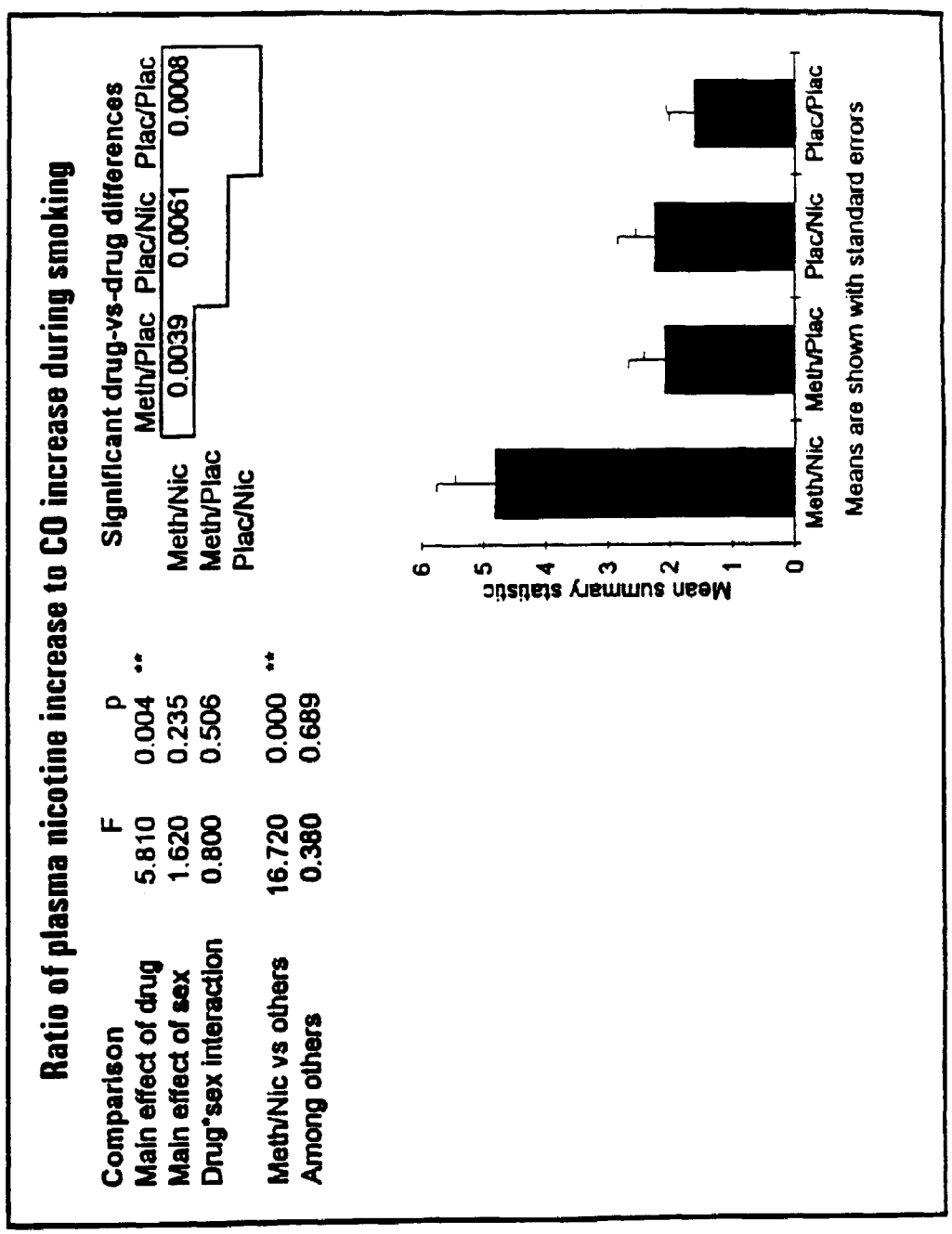
FIG. 10 illustrates the ratio of increased plasma nicotine to increased breath carbon monoxide in Example 9.

FIG. 10 illustrates the ratio of the increased plasma nicotine concentration to increased breath carbon monoxide concentration over the 90 minute free smoking period. In other words, this Figure illustrates the measure of potential reduction in smoke exposure that might occur while dependent smokers replenish their systemic plasma nicotine content. As illustrated, the methoxsalen/nicotine treatment stands apart from all three of the other treatments and from their mean, more than doubling the gain in nicotine per unit of increase in breath carbon monoxide concentration.

Figure 11:
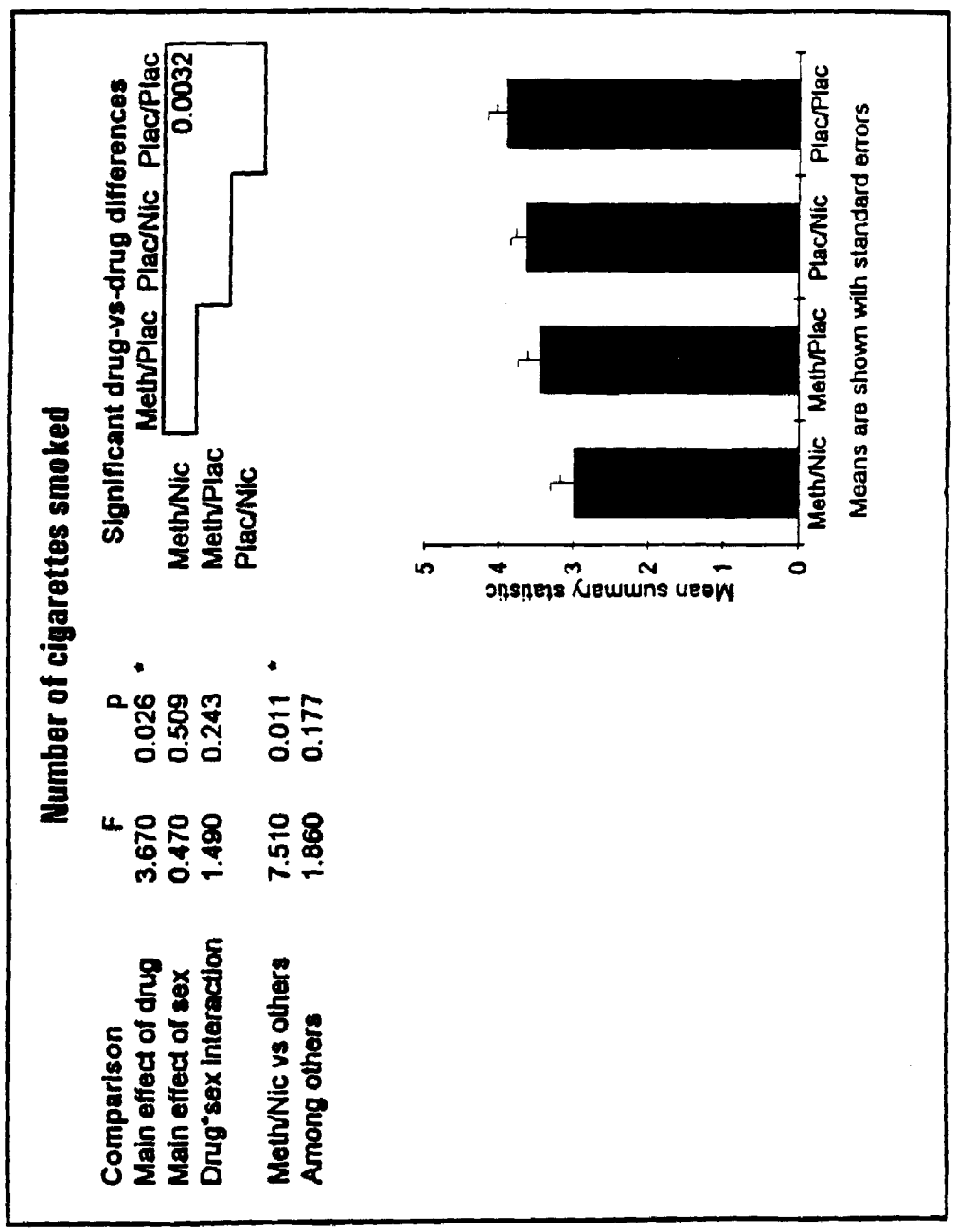
FIG. 11 illustrates mean number of cigarettes consumed during the smoking period in Example 9.

FIG. 11 illustrates the commonly used measure of smoking: the mean number of cigarettes smoked during the 90 minute period. As illustrated, the combined methoxsalen/nicotine treatment is associated with the least smoking, however number of cigarettes consumed is an insensitive measure of smoke exposure and smoking behaviour compared to breath carbon monoxide concentration.

Figure 12:
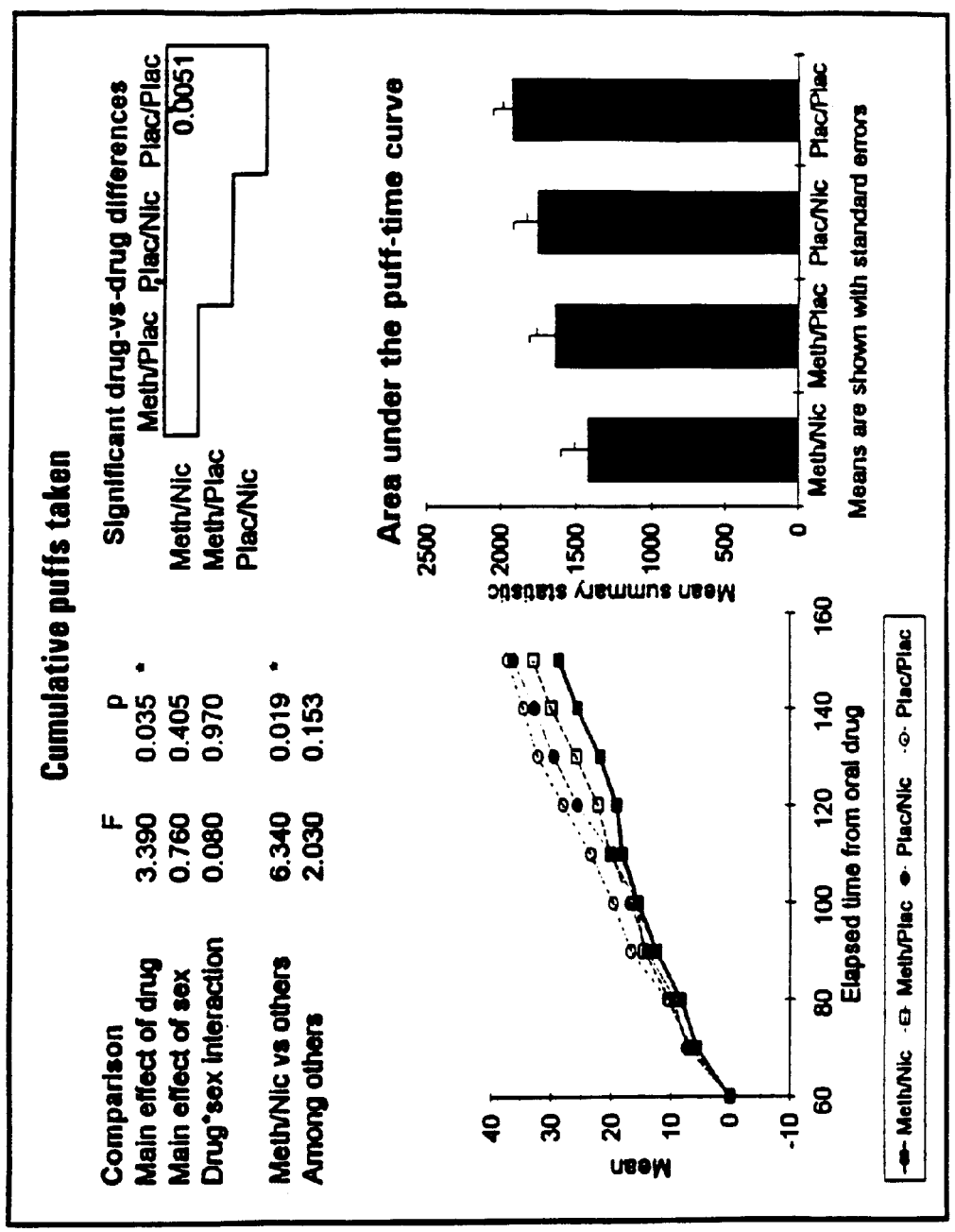
FIG. 12 illustrates the mean number of cigarette puffs taken in each 10-min. period during the smoking period in Example 9.

FIG. 12 illustrates the mean cumulative number of puffs taken by the end of each 10 minute period during the 90 minute free smoking period, and the data is summarized by the area under this curve. This area would increase if either the total number of puffs increased, or if the same number were consumed earlier thereby shifting the curve to the left. As illustrated, the methoxsalen/nicotine treatment is associated with the fewest cumulative number of cigarette puffs.

Figure 13:
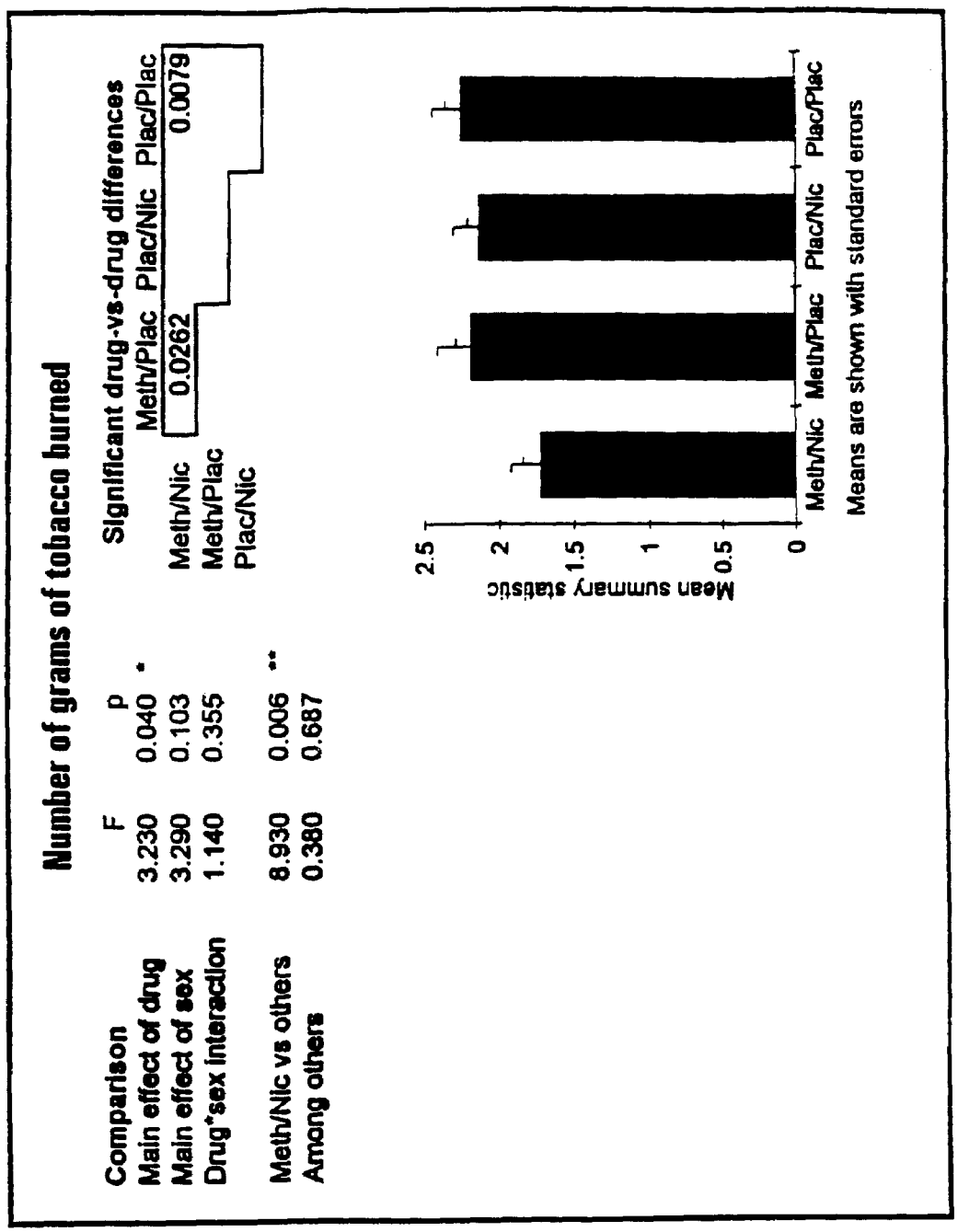
FIG. 13 illustrates the mean latency period between the first two cigarettes in Example 9.

FIG. 13 illustrates that the number of grams of tobacco burned is significantly less in the methoxsalen/nicotine treatment group. Again, this measure is less sensitive than direct measures of smoking behaviour and smoke exposure (e.g., breath carbon monoxide concentration and nicotine/breath carbon monoxide concentration).

Figure 14:
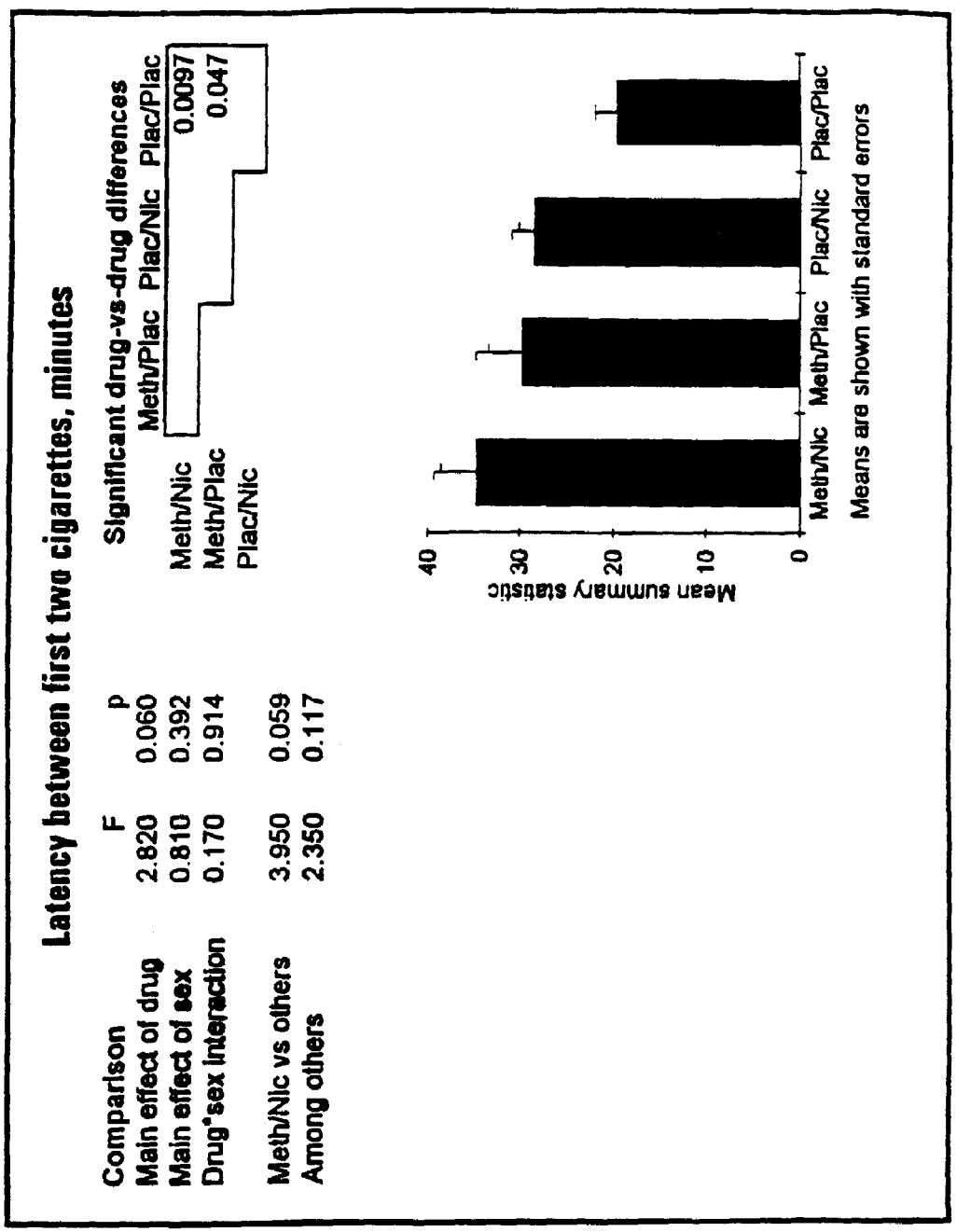
FIG. 14 illustrates the mean grams of tobacco burned in Example 9.

FIG. 14 illustrates that the inhibition of CYP2A6 metabolism of nicotine achieves the reduction in breath carbon monoxide by changing nicotine-regulated smoking behaviour. The latency between cigarettes is significantly prolonged by the combined methoxsalen/nicotine treatment.

In summary, the results illustrated in FIGS. 9-14 show a modification in smoking behaviour by subjects who were treated with a combination of methoxsalen and nicotine. Specifically, key objective indicators such as plasma nicotine concentration and breath carbon monoxide were significantly reduced compared to the other treatment regimens.

CYP2A6 metabolizes approximately 75% of nicotine in vivo. Tobacco-dependent smokers regulate their smoking to maintain nicotine levels; CYP2A6 inhibition should decrease nicotine metabolism, decrease smoking and smoke exposure (e.g. breath CO). Overnight nicotine-abstinent dependent smokers (6 males, 5 females) smoked one cigarette followed by one of four oral drug combinations in crossover counter-balanced order: methoxsalen 30 mg (CYP2A6 inhibitor K; =0.2 µM) or placebo with either nicotine 4.0 mg or placebo. Sixty minutes later, subjects started 90 mins of ad libitum smoking. Subjects receiving methoxsalen with oral nicotine smoked less than in the placebo/placebo (e.g. breath CO 50% less increase; latency to the second cigarette 83% increase, number of cigarettes smoked 24% decrease; tobacco burned (grams) 24% decrease, total number of puffs taken decrease 25% [all p<0.05]). In addition, on several measures (e.g. latency to second cigarette) the rank order of response was methoxsalen/nicotine>methoxsalen/placebo>placebo/nicotine>placebo/placebo suggesting a methoxsalen effect on systemic clearance of nicotine. CYP2A6 inhibition alone or combined with oral nicotine decreases smoking and could have a role in tobacco smoking cessation, exposure reduction or relapse prevention strategies.

Example 10

Figure 15:
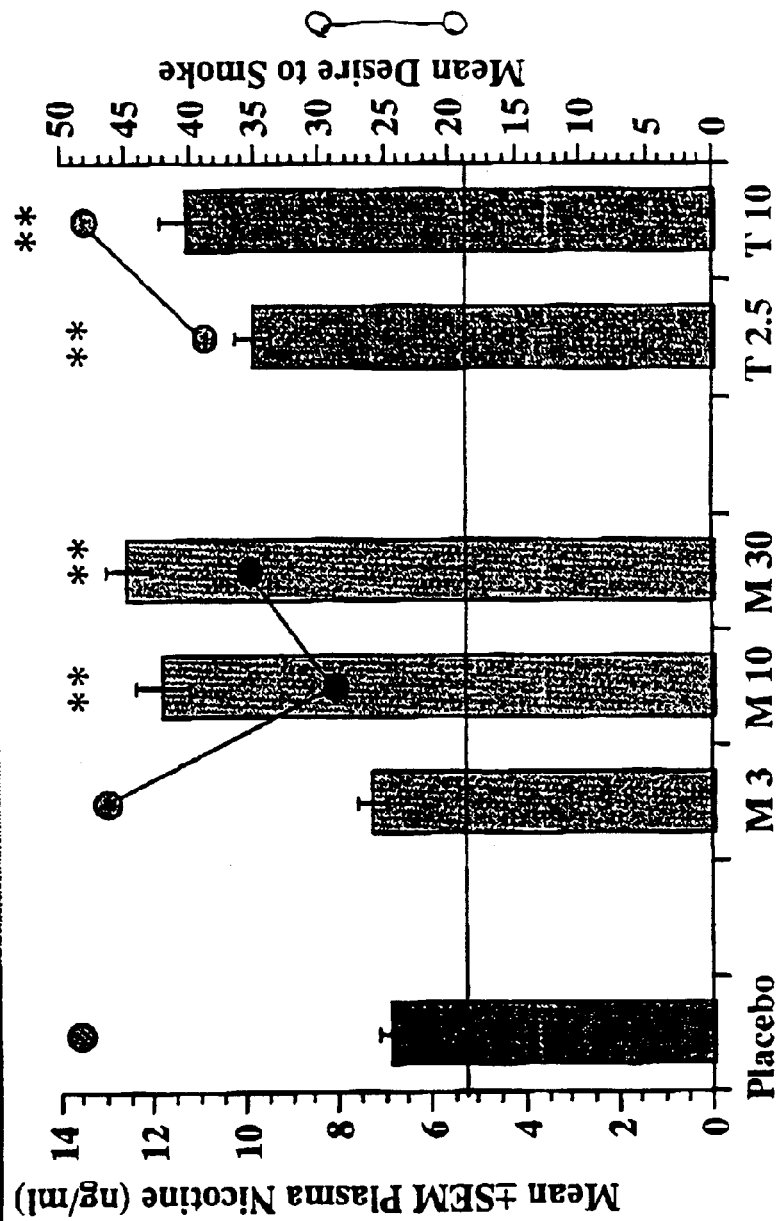
FIG. 15 illustrates the effect of CYP2A6 inhibitors methoxsalen and tranylcypromine on increasing the bioavailability of nicotine supplied orally, with concomitant reduction in the desire to smoke.

Inhibitors Of Nicotine's Metabolism: Potential New Treatments For Tobacco Dependence Nicotine is inactivated by CYP2A6 to cotinine. As nicotine bioavailability is low (20-35%), an oral nicotine replacement is feasible. In vitro inhibition of nicotine metabolism was studied in expressed CYP2A6 using tranylcypromine, methoxsalen, and as inhibitors ($K_i$=0.05-6 µM). In dependent smokers methoxsalen, 30-50 mg orally 30 min prior to nicotine 31 µg/kg subcutaneously (3 doses, hourly), increased the 8-hour mean plasma nicotine by 49% (p<0.01) while coumarin (225 mg hourly×6) increased it by 15% (p<0.05) compared to placebo. Using methodology described above, studies conducted in regular smokers (n=7-12) given nicotine (4.0 mg p.o.) alone and concurrently with placebo, methoxsalen (3 mg, 10 mg or 30 mg) or tranylcypromine (2.5 mg or 10 mg) significantly increased the plasma nicotine compared to placebo (see FIG. 15). Specifically, methoxsalen 10 and 30 mg (M10 and M30, FIG. 15) and tranylcypromine 2.5 and 10 mg (T2.5 and T10, FIG. 15) produced approximate 100% increases in plasma nicotine (p<0.01). In addition, these increases in oral nicotine bioavailability were associated with a significant (p<0.05) decrease in desire to smoke for M10 and M30 and T2.5 (p=0.17) (see FIG. 15, solid circles).

From these studies it is evident that methoxsalen and tranylcypromine in doses ¼ and ⅛, respectively, of their current therapeutic doses used for treating psoriasis and depression, respectively, can be used to inhibit nicotine first-pass metabolism and systemic metabolism. Other CYP2A6 inhibitors and their isomeric forms can be expected to do the same.

Example 11

Extraction of *Hypericum*

The following procedures were used to prepare an extract of *Hypericum perforatum*:

An extraction mixture of 10 *Hypericum* capsules (0.3% hypericin) and 50 ml of 80% methanol (water 20%, v/v) was placed in a beaker (125 ml). In one protocol the extraction was carried out using cold methanol. In a second protocol, the extraction mixture was placed in a water-bath and heated until boiling (about 80° C.). The mixture was kept boiling for 30 min, keeping the volume to 50 ml by adding methanol, then cooled down at room temperature, and centrifuged at 3,000 g for 5 min. The resulting extract was then blown to dryness and resuspended in trisbuffer pH 7.4.

Example 12

Effect of *Hypericum* Extracts on CYP2A6 Activity

Nicotine metabolism was monitored in vitro. Inhibitor assessment was carried out by comparing the assay including 50 µl tris buffer with the extracts prepared in Example 11 (50 µl, diluted in tris buffer). Human liver microsomes or CYP2A6 microsomes were used. The concentration of inhibitor in *Hypericum* was calculated on the basis of an apparent molecular weight of the inhibitor of 504 and a concentration of 0.3% active material in the plant material when diluting to yield concentrations of 20, 10, 5, 1, 0.1 and 0.01 and 0.01 µM.

Incubation Mixture:
  Substrate 80 µM (50 µl tris buffer)
  NADPH1 mM (50 µl tris buffer)
  Microsomes 80 µg (30 µl tris buffer)
  Cytosol (rat) 20 µl (tris buffer)
  Tris buffer 50 µl (pH7.4)
  Final volume 200 µl Incubation Procedure:

The incubation was carried out at 37° C. for 30 min. An internal standard (50 µl, caffeine, 0.05 mg/ml) was added to the incubation mixture, followed by DCM (1 ml). The mixture was shaken for 10 min and centrifuged for 5 min at 3,000 g. The top layer was aspirated. HC1 (0.01 N, 100 µl) was added, followed by shaking for 1 min, then centrifuge for 5 min at 3,000 g. 30 µl of the HCl layer was injected for HPLC.

HPLC Conditions

Column: Supelco; 5-8347; LC-8-DB; 150×4.6 mm; 5 µm
I: 260 nm
Flowrate: 1.3 ml/min
Mobile phase: 1000/120 (citric buffer/acetonitrile, v/v)
Citric buffer: Citric Acid 7.14 g (0.34 M)
  $KH_2PO_4$ 4.627 g (0.34 M)
  1-Heptane sulphonate 670 mg
  Triethylamine 5 ml
  Final volume 1000 ml
  Adjust the pH to 4.40 with 5 N KOH Retention Times (min):
  2.2 (nicotine iminium ion)
  2.7 (nicotine)
  3.4 (continine)
  3.9 (caffeine) (internal standard)

Figure 16:
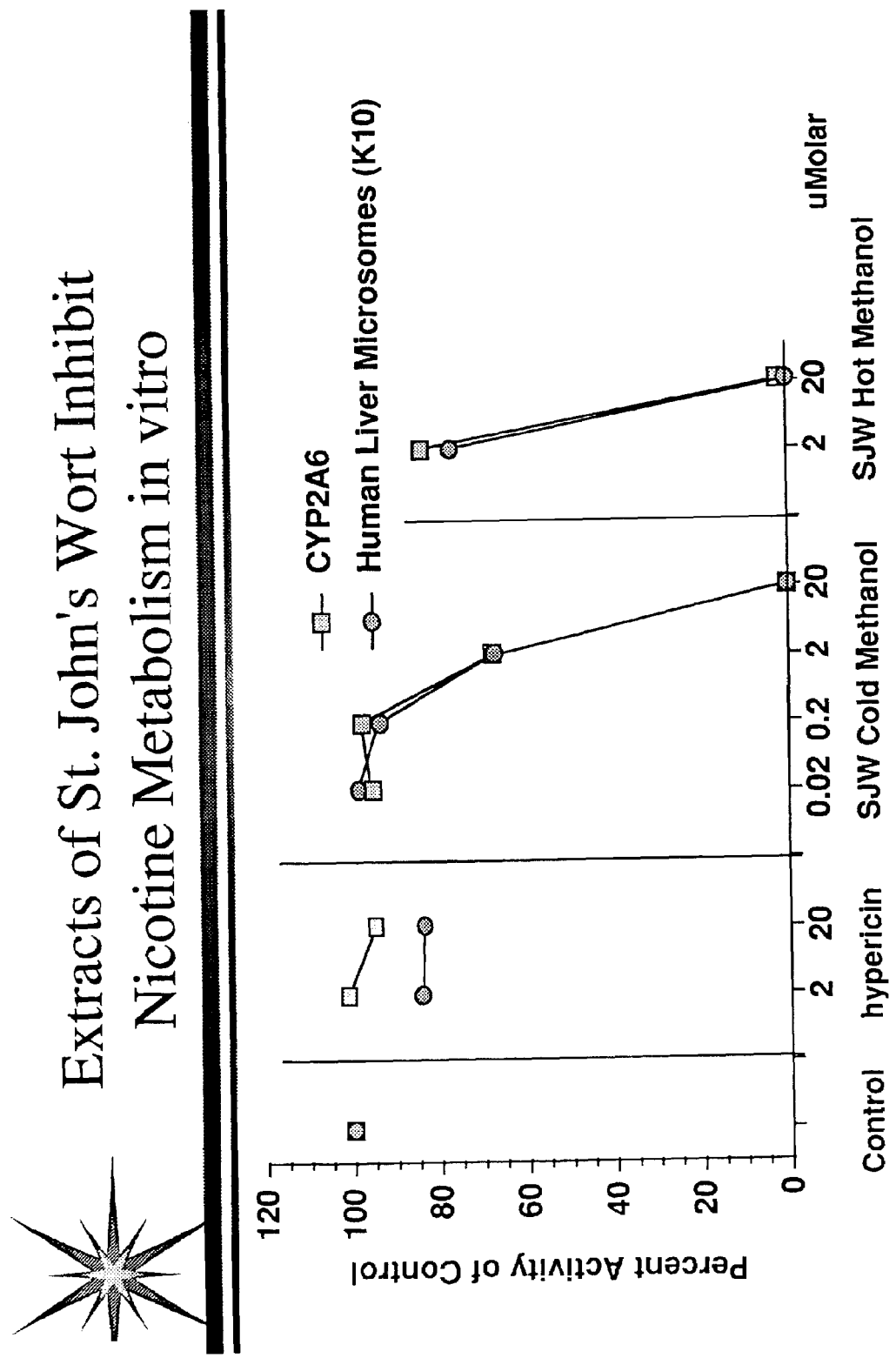
FIG. 16 is a graph illustrating the effect of *Hypericum* extracts on nicotine metabolism by expressed human cDNA CYP2A6.
Figure 17:
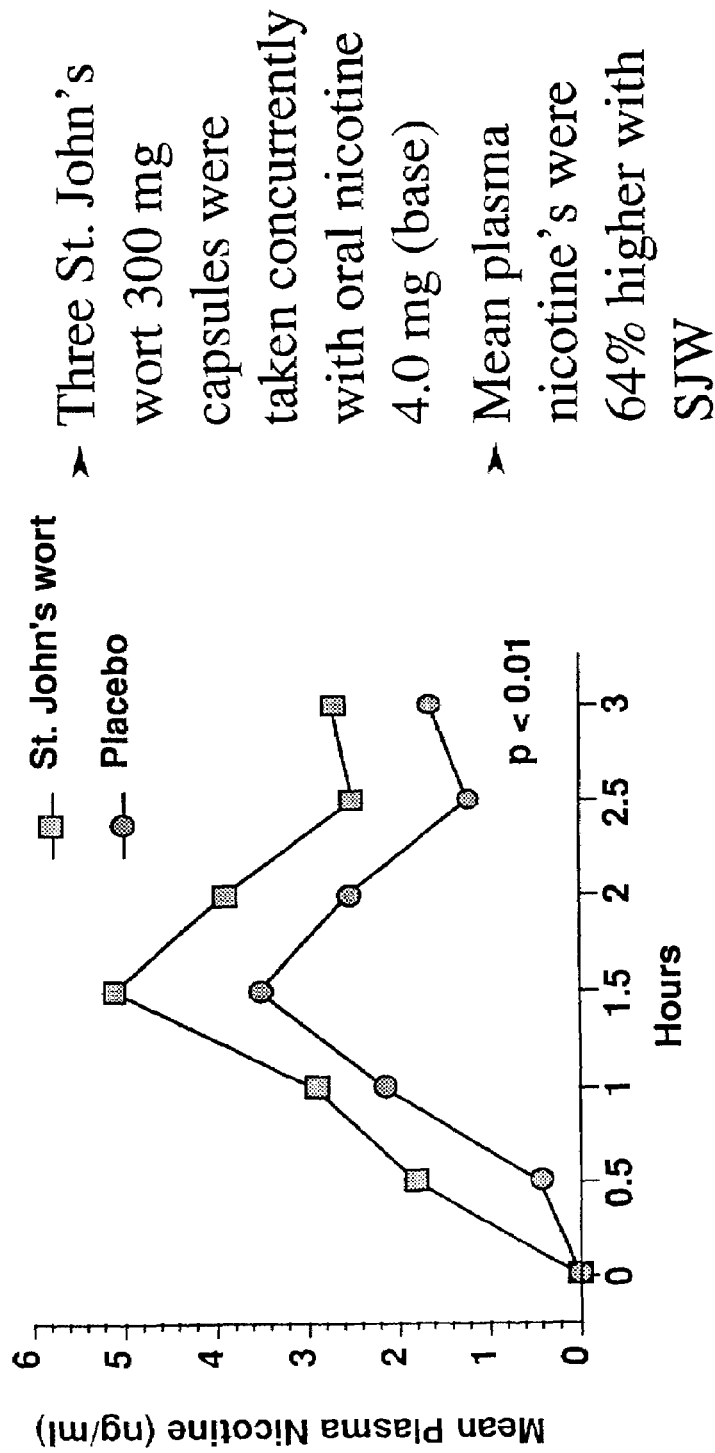
FIG. 17 is a graph showing the mean plasma concentration of nicotine versus time, in the presence of St. John's Wort or a placebo.

FIG. 16 demonstrates the inhibition of nicotine metabolism with (1) cold methanol extract of *Hypericum*; (2) a hot methanol extract of *Hpericum*; (3) purified Hypericin; and (4) a negative control. The results indicate that both methanol extracts of *Hypericum* can inhibit CYP2A6 activity.

Example 13

Effect of St. John' Wort on Nicotine Metabolism

Twelve subjects received placebo or 3 St. John's Wort capsules 300 mg plus oral nicotine 4.0 mg as base orally. Blood samples were taken at designated times over 3 hours.

Figure 18:
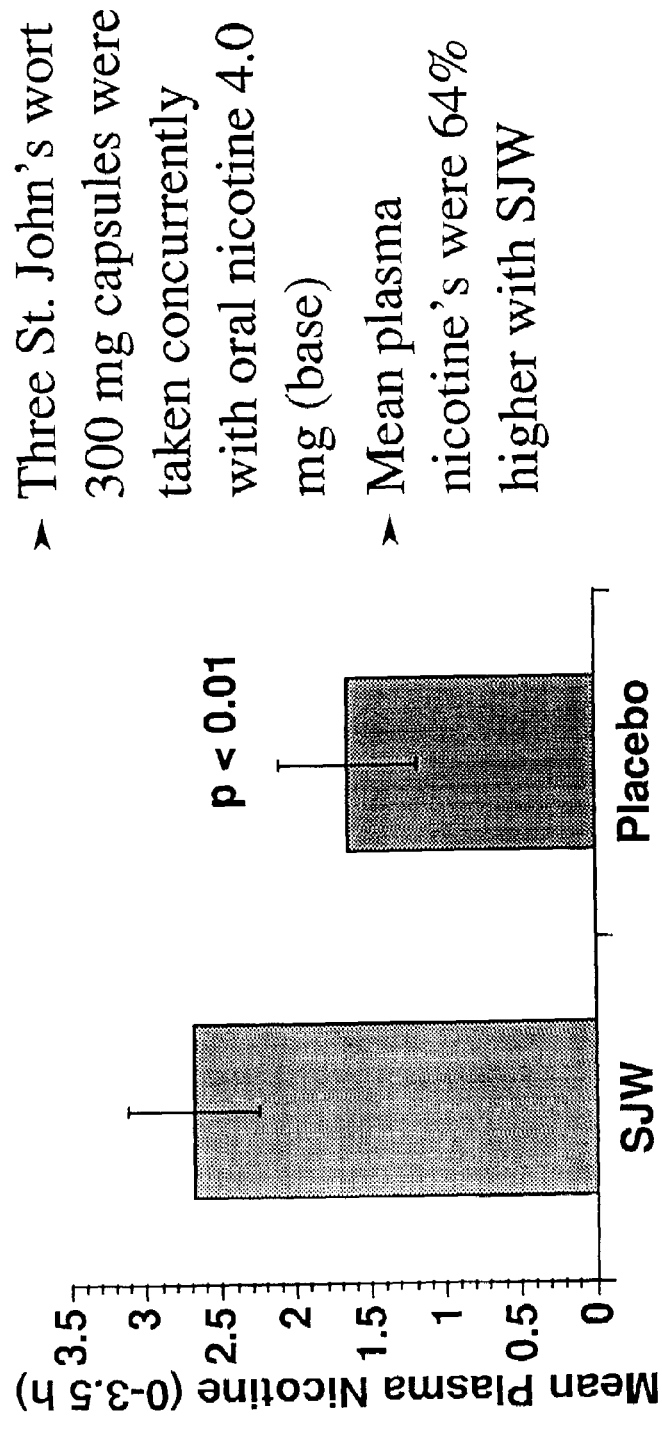
FIG. 18 is a bar graph showing the mean plasma concentration of nicotine in the presence of St. John's Wort or a placebo.
Figure 19:
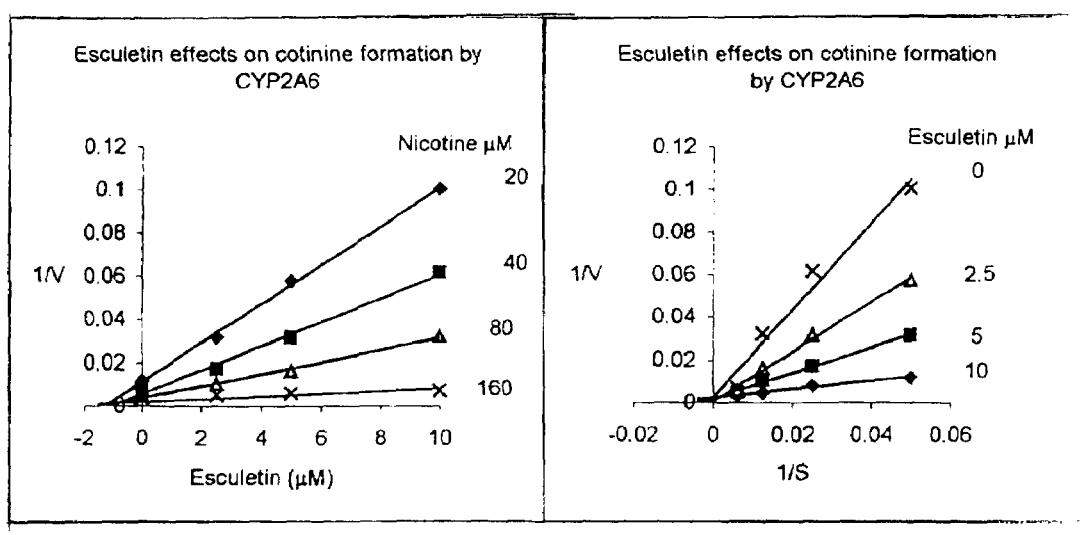
FIG. 19 are graphs illustrating effect of esculetin on nicotine metabolism by human liver micorsomes.
Figure 19:
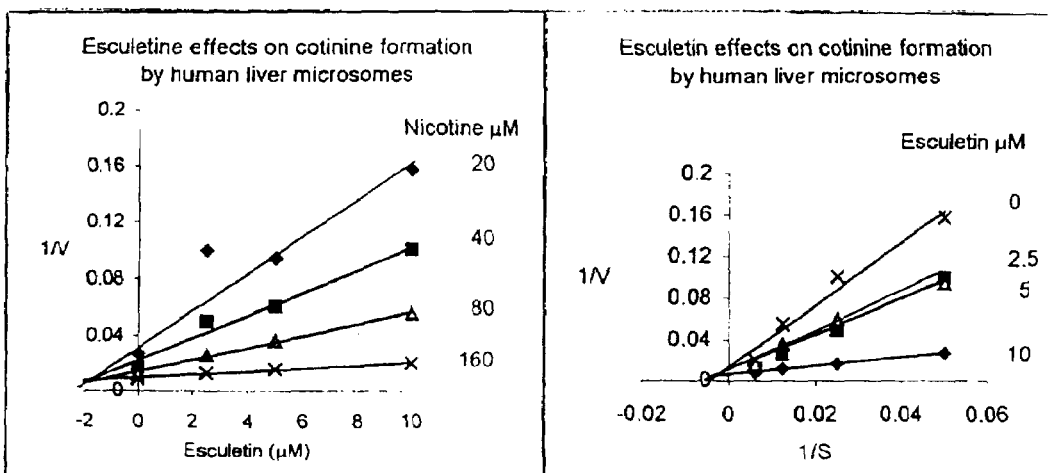

The results shown in FIGS. 18 and 19 demonstrate that St. John's Wort increases the bioavailability of nicotine in vivo. The mean plasma nicotine concentrations were 64% higher after St. John's Wort.

Example 14

Effect of Esculetin on CYP2A6 Activity

Esculetin, a compound found in *Cichorium intybus* and *Bougainvllra spectabillis,* was tested for its ability to inhibit nicotine metabolism by CYP2A6 using the methods set forth in Example 12.

The results, shown in FIG. 19, demonstrate that esculetin is a potent inhibitor of CYP2A6.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

TABLE 1

|  | Genotype Frequency | | | Average Number of Cigarettes Smoked Per Day | | | | | |
|---|---|---|---|---|---|---|---|---|---|
|  | | | | TD | | | AT | | |
|  | NTD | TD | AT | Males | Females | Total | Males | Females | Total |
| Age | 28.3 | 31.2 | 37.8 | 31.1 | 31.4 | 31.2 | 37.2 | 41.4 | 37.8 |
| wt/wt | 130 | 114 | 62 | 26.1 | 19.5 | 23.2 | 28.9 | 27.8 | 28.7 |
| wt/mut | 31 | 17 | 7 | 19.3 | 18.7 | 19.1 | 29.7 | 50.0 | 32.6 |
| mut/mut | 2 | 2 | 1 | 22.5 | — | 22.5 | 25 | — | 25 |
| n | 163 | 133 | 70 | 76 | 57 | 133 | 60 | 10 | 70 | wt/wt: CYP2A6*1/CYP2A6*1
wt/mut: CYP2A6*1/CYP2A6*2 + CYP2A6*1/CYP2A6*3
mut/mut: CYP2A6*2/CYP2A6*2

We claim:

1. A method of stopping smoking of tobacco or reducing the amount of tobacco smoked comprising contemporaneously administering to an individual in need thereof an effective amount of nicotine and an effective amount of selegiline.

2. The method according to claim 1, wherein said nicotine is formulated for oral administration.

3. The method according to claim 1, wherein said selegiline and said nicotine are formulated in a single composition.

4. The method according to claim 1, further comprising administering an inhibitor of CYP2B6 to said individual contemporaneously with said selegiline and said nicotine.

5. The method according to claim 1, wherein said selegiline or nicotine are formulated for oral, topical, rectal, parenteral, local, inhalant or intracerebral administration.

6. The method according to claim 5, wherein said topical administration is via a transdermal route.

7. The method according to claim 1, wherein said nicotine is formulated for oral administration and said selegiline is formulated for topical administration.

8. The method according to claim 7, wherein said nicotine is formulated for topical administration and said selegiline is formulated for oral administration.

9. The method according to claim 1, wherein said selegiline or nicotine are administered by way of a controlled or slow release system.

* * * * *